(12) United States Patent
Fournillier et al.

(10) Patent No.: US 8,057,162 B2
(45) Date of Patent: *Nov. 15, 2011

(54) COMPOSITION COMPRISING THE POLYPROTEIN NS3/NS4 AND THE POLYPEPTIDE NS5B OF HCV, EXPRESSION VECTORS INCLUDING THE CORRESPONDING NUCLEIC SEQUENCES AND THEIR THERAPEUTIC USE

(75) Inventors: Anne Fournillier, Lyons (FR); Genevieve Inchauspe, Lyons (FR); Jean-Daniel Abraham, Strasbourg (FR); Maria Dimitrova-Tchomakov, Strasbourg (FR); Marie Parnot, Strasbourg (FR)

(73) Assignees: Transgene S.A. (FR); Institut National de la Sante et De La Recherche Medicale, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/472,330

(22) Filed: May 26, 2009

(65) Prior Publication Data

US 2010/0008941 A1 Jan. 14, 2010

Related U.S. Application Data

(63) Continuation of application No. 10/559,431, filed as application No. PCT/FR2004/050214 on Jun. 4, 2004, now abandoned.

(30) Foreign Application Priority Data

Jun. 5, 2003 (FR) ...................................... 03 06772

(51) Int. Cl.
*A61K 48/00* (2006.01)
*C12N 15/63* (2006.01)
(52) U.S. Cl. ..................... 415/44; 424/228.1; 435/320.1
(58) Field of Classification Search .................. None
See application file for complete search history.

(56) References Cited

U.S. PATENT DOCUMENTS

| | | | |
|---|---|---|---|
| 6,312,889 B1 | 11/2001 | Houghton et al. | |
| 6,562,346 B1 * | 5/2003 | Paliard et al. .............. | 424/189.1 |
| 6,986,892 B1 | 1/2006 | Coit et al. | |
| 7,052,696 B2 | 5/2006 | Fields et al. | |
| 7,285,539 B2 * | 10/2007 | Paliard et al. .............. | 514/44 R |
| 7,695,960 B2 * | 4/2010 | Inchauspe et al. ......... | 435/320.1 |
| 2007/0269460 A1 | 11/2007 | Inchauspe et al. | |

FOREIGN PATENT DOCUMENTS

WO    WO 01/30812    5/2001

OTHER PUBLICATIONS

Pancholi et al., "DNA Immunication with Hepatitis C Virus (HCV) Polycistronic Genes or Immunization by HCV DNA Priming-Recombinant Canarypox Virus Boosting Induces Immune Responses and Protection from Recombinant HCV-Vaccinia Virus Infection in HLA-A2.1—Transgenic Mice," *Journal of Virology*, 2003, vol. 77, No. 1, pp. 382-390, American Society for Microbiology, Washington, D.C.
Cho et al., "Enhanced cellular immunity to hepatitis C virus nonstructural proteins by codelivery of granulocyte macrophage-colony stimulating factor gene in intramuscular DNA Immunication," *Vaccine*, 1999, vol. 17, pp. 1136-1144, Elsevier Science, Amsterdam, Holland.
Clarke et al., "Molecular virology of hepatitis C virus," *Journal of General Virology*, 1997, vol. 78, pp. 2397-2410, American Society for Microbiology, Washington, D.C.
Inchauspe et al., "Development of a hepatitis C virus vaccine," *Clin. Liver Dis.*, 2003, vol. 7, pp. 243-259, Elsevier. Amsterdam, Holland.
Hsu et al., "Prospects for a Hepatitis C Virus Vaccine," *Clin. Liver Dis.*, 1999, vol. 3, pp. 901-915, Elsevier. Amsterdam, Holland.
Purcell et al., "The Hepatitis C Virus: Overview," *Hepatology*, Sep. 1997, vol. 26, pp. 11A-14A, American Association for the Study of Liver Diseases, Alexandria, Virginia.
Krieger et al., "Enhancement of Hepatitis C Virus RNA Replication by Cell Culture-Adaptive Mutations," *J. Virol.*, 2001, vol. 75, No. 10, pp. 4614-4624, American Society for Microbiology, Washington, D.C.
Hadziyannis et al., "Peginterferon-α2a (40 kDa) for chronic hepatitis C," *Expert Opinion on Pharmacotherapy*, Apr. 2003, vol. 4, No. 4, pp. 541-551, Informa Healthcare, London, England.
Paul et al., "Tumor gene therapy by MVA-mediated expression of T-cell-stimulating anitbodies," *Cancer Gene Therapy*, 2002, vol. 9, pp. 470-477, Nature Publishing Group, London, England.
Fournillier et al., "An accelerated vaccine schedule with a polyantigenic hepatitis C virus MVA-based candidate vaccine induces potent, long lasting and in vivo cross-reactive T cell responses," *Vaccine*, 2007, vol. 25, pp. 7339-7353, Elsevier Ltd., Amsterdam, Holland.

\* cited by examiner

*Primary Examiner* — Bao Li
(74) *Attorney, Agent, or Firm* — Buchanan Ingersoll & Rooney PC

(57) ABSTRACT

The invention relates to a peptidic compound containing a polyprotein NS3/NS4 of a hepatitis C virus and a polypeptide NS5b of hepatitis C virus. Said invention also relates to expression vectors such as adenovirus and poxvirus in which nucleic sequences coding for the polyprotein NS3/NS4 and the polypeptide NS5b. The inventive compound can be used for a therapeutic application.

21 Claims, 18 Drawing Sheets

Figure 1 (continuation)

Figure 1 (continuation)

Figure 1 (continuation)

Figures 2, 2A:
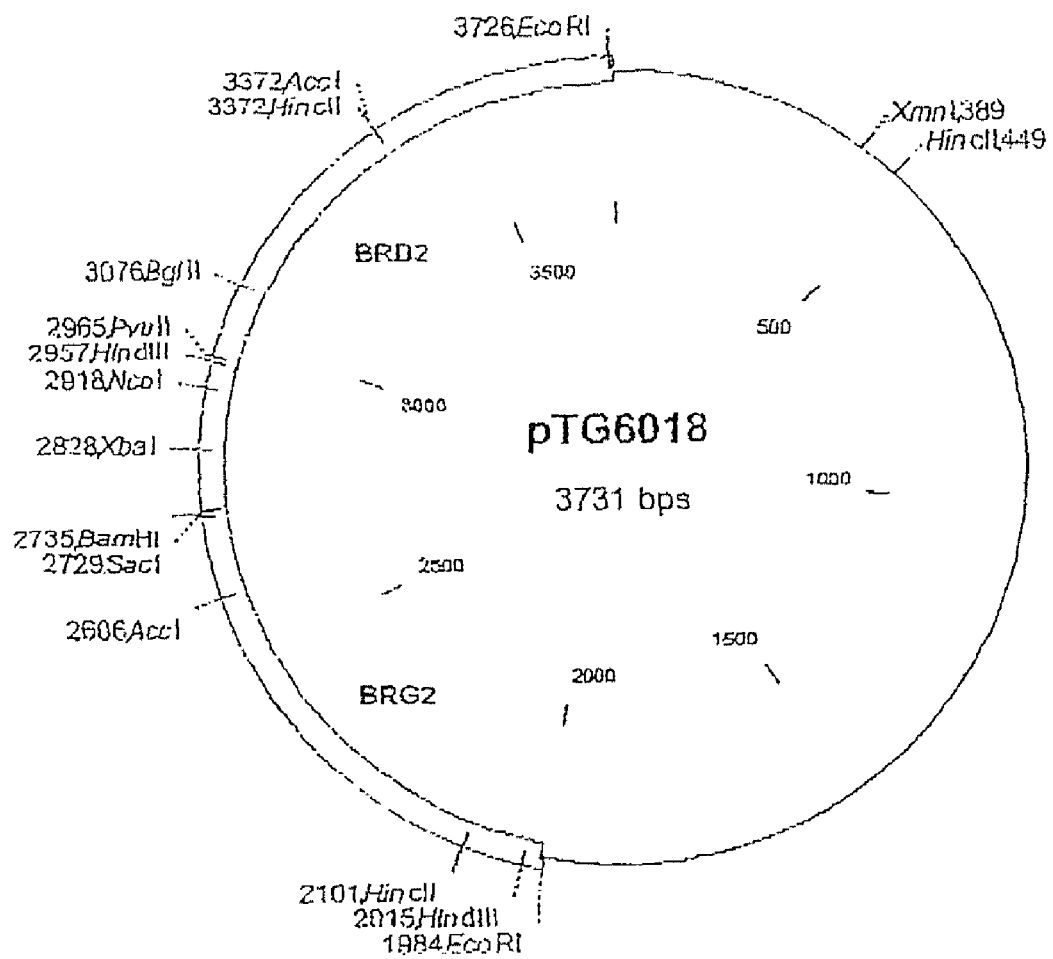

Figure 2 (continuation)

Figure 2 (continuation)

Figure 2 (continuation)

Figure 2 (continuation)

Figure 2 (continuation)

COMPOSITION COMPRISING THE POLYPROTEIN NS3/NS4 AND THE POLYPEPTIDE NS5B OF HCV, EXPRESSION VECTORS INCLUDING THE CORRESPONDING NUCLEIC SEQUENCES AND THEIR THERAPEUTIC USE

The present invention relates to the field of prophylactic and therapeutic vaccination directed against the hepatitis C virus (HCV). It relates in particular to a novel composition containing a polyprotein corresponding to the two collinear proteins NS3 and NS4 (hereafter called polyprotein NS3/NS4) and a polypeptide constituted by NS5b, the vectors, such as adenovirus or poxvirus, capable of expressing this composition and their use as vaccine.

Hepatitis C is the major cause of transfusion-acquired hepatitis. Hepatitis C can also be transmitted by other percutaneous routes, for example by injection of drugs by intravenous route. The risk of contamination of health professionals is moreover not negligible. Sexual transmission has been described.

Hepatitis C differs from other forms of liver diseases associated with viruses, such as hepatitis A, B or D. The infections by the hepatitis C virus (HCV or HCV) are mostly chronic resulting in diseases of the liver, such as hepatitis, cirrhosis and carcinoma in a large number of cases (5 to 20%) and represents 30% of the hepatic transplants in developed countries.

Although the risk of transmission of the virus by transfusion has diminished owing to the introduction of screening tests in the 1990s, the frequency of new HCV infections remains high. By way of example, a recent study indicates that today there are still 10,000 to 15,000 new cases of infection per year in France (S. Deuffic et al., Hepatology 1999; 29: 1596-1601). Currently, approximately 170 million people worldwide are chronically infected by HCV (Hepatitis C: Global prevalence (update), 2000, Weekly Epidemiological Record, Vol 75(3)). The high-risk populations are principally hospital staff and intravenous-drug users, but there are asymptomatic blood donors who do not belong to these high-risk groups and in whom circulating anti-HCV antibodies have been found. For the latter, the infection route has not yet been identified. HCV infections therefore exist (estimated at between 5 and 10%), known as sporadic infections, the etiology of which is unknown and which cannot be controlled.

HCV was the first hepatotropic virus isolated by means of molecular biology techniques. The viral genome sequences were cloned before the viral particle was visualized.

HCV belongs to a new genus of the Flaviviridae family, the hepaciviruses. It is a positive single-strand RNA virus, of 9.5 kb, which is replicated by a complementary RNA copy and the translation product of which is a polyprotein precursor of approximately 3,000 amino acids. The 5' end of the HCV genome corresponds to an untranslated region adjacent to the genes that code for the structural proteins, the core protein of the nucleocapsid, the two envelope glycoproteins, E1 and E2, and a small protein called p7. The 5' untranslated region and the gene core are relatively well preserved in the different genotypes. The envelope proteins E1 and E2 are encoded by regions that are more variable from one isolate to another. The protein p7 is an extremely hydrophobic protein, which may constitute an ion channel. The 3' end of the HCV genome contains the genes that code for the non-structural proteins (NS2, NS3, NS4, NS5) and for a 3' non-coding region possessing a well-conserved domain (Major M E, Feinstone S M, Hepatology, June 1997, 25 (6): 1527-1538).

At present, the most effective therapy for the treatment of hepatitis C combines pegylated interferon and ribavin (Manns M P et al., The Lancet, 22 Sep. 2001, Vol. 358, 958-965). Whilst this therapy is particularly effective in the case of patients infected by viral strains belonging to the genotypes 2 and 3, it still has only a limited effect on the genotypes 1a, 1b and 4 (Manns M P, op. cit.). Less than 50% of the treated patients become "long-term responders". Moreover, this therapy is an expensive intervention (10,000 to 15,000 euros/patient/year) and is associated with toxic effects. In fact, 5 to 10% of the patients are obliged to stop treatment before the end.

It is therefore necessary to develop a vaccine composition targeting all the genotypes.

Several studies now show that the control of an infection caused by HCV either naturally (spontaneous resolution), or after treatment (therapeutic resolution) is associated with the induction or potentialization of cell-mediated immune responses involving the T-CD4$^+$ and T-CD8$^+$ lymphocytes (as described for example in LECHNER, F. et al., Eur. J. Immunol., 30: 2479-2487 (2000) and in Thimme R. et al., 2001, J. Exp. Med., 194 (10): 1395-1406).

The molecules of the major histocompatibility complex (MHC, also known as HLA in humans) are referred to as class I or class II. The class I molecules are expressed on virtually all of the nucleated cells and are able to present epitopes or peptides to the CD8$^+$ cytotoxic T lymphocytes (CTL). The class II molecules are able to present epitopes to the CD4$^+$ T cells, but their expression is restricted to antigen-presenting cells.

The vaccines against the hepatitis C virus currently envisaged are based on the use of adjuvant recombinant proteins, peptides, expression vectors among which there can be mentioned vectors of viral or bacterial origin or of naked DNA. In this case, one or more viral proteins or one or more genes coding for these viral proteins are used.

When several viral proteins or one or more genes coding for these viral proteins are selected, the latter are often constituted either by some or all of the structural proteins (Makimura et al., 1996, Vaccine, 14: 28-34; Fournilier A. et al., 1999, J. Virology, 73: 7497-7504), or by individual non-structural proteins or comprising at least two contiguous proteins (Brinster et al., 2001, Hepatology, 34: 1206-1217), or by a mixture of structural and non-structural proteins (Pancholi et al., 2003, J. Virology, 77: 382-390).

The Patent Application WO99/38880 describes the use of three genes coding separately for the three proteins NS3, NS4 and NS5 (a and b) in a vaccine composition comprising three DNA vaccines each expressing these three proteins separately. The authors show the induction of T lymphocytes specific to the three antigens in mice. Only the vaccine expressing NS5a and b has been tested in vivo in a protection test.

The Patent Application WO01/30812 describes the use of a fusion protein constituted by the non-structural proteins NS3, NS4 and NS5a, if necessary in combination with the non-structural protein NS5b. The authors have indicated that this combination made it possible to activate the HCV-specific T cells. This patent application simply describes the ability of vaccine formulations (naked-DNA, recombinant-adenovirus or recombinant-vaccinia-virus type) expressing the fusion protein NS3, NS4, NS5a or the protein NS5a to induce specific immune responses mediated by specific T lymphocytes.

The Applicant has now demonstrated, against all expectation, that the particular combination of the non-structural proteins NS3, NS4 and NS5b, NS3 and NS4 being expressed colinearly had a better immunogenic power and protective power superior to that obtained with a vaccine also including, apart from these non-structural proteins, the protein NS5a and/or other structural proteins of HCV such as core, E1 or E2, and had an effect on the ability of cells originating from patients infected by viral strains to induce specific immune responses.

Thus, an object of the present invention is a peptide composition comprising a polyprotein NS3/NS4 of the hepatitis C virus, as well as a polypeptide NS5b of the hepatitis C virus.

An object of the invention is also the vectors including the nucleotide sequences coding for this peptide composition, such as the adenoviruses and poxviruses, as well as microorganisms or host cells transformed by these vectors.

An object of the invention is finally the antibodies directed against the peptide composition of the invention, as well as the use of the peptide composition, vectors and antibodies for the preparation of a medicament intended for the inhibition or control of an infection caused by the hepatitis C virus, and in a vaccine composition.

The present invention therefore proposes a novel peptide composition constituted by a polyprotein NS3/NS4 and a polypeptide NS5b of HCV, which composition has the ability to stimulate a cell-mediated immune response specific to HCV, such that it is useful in the field of prophylactic and therapeutic vaccination directed against the hepatitis C virus.

The polyprotein NS3/NS4 of the peptide composition of the invention is constituted by the protein NS3 and the protein NS4a and b, without interruption in the peptide sequence, as in the native polyprotein. In fact, as indicated previously, the HCV genome contains a single open reading frame that is transcribed into a polyprotein. This HCV polyprotein can be cleaved in order to produce at least ten distinct parts, in the order $NH_2$-Core-E1-E2-p7-NS2-NS3-NS4a-NS4b-NS5a-NS5b-COOH.

The protein NS3 is a protein of 630 amino acids, which appears approximately from amino acid 1027 to amino acid 1657 of the polyprotein. The protein NS4, a protein of 314 amino acids, appears approximately from amino acid 1658 to amino acid 1972 (numbering with respect to HCV-1) (Choo et al., 1991, Proc. Natl. Acad. Sci., vol 88: 2451-2455). The polyprotein NS3/NS4 therefore appears approximately from amino acid 1027 to amino acid 1972.

As regards the polypeptide NS5b also contained in the composition of the invention, it is constituted by 590 amino acids and appears approximately from amino acid 2421 to amino acid 3011 of the polyprotein (Choo et al., 1991, op. cit.).

The protein NS3 comprises two distinct structural domains, namely an N-terminal domain endowed with an active serine protease activity that is involved in the maturation of the viral polyprotein, and a C-terminal domain comprising a helicase activity associated with an NTPase activity that plays a role in the replication of the viral genome.

By "polyprotein NS3/NS4" and "polypeptide NS5b", is of course meant the polyproteins and polypeptides having the native amino acid sequences, originating from any HCV strain and isolate, as well as their analogues, muteins and homologues.

By "analogues" or "muteins" of the polyprotein and of the polypeptide, is meant the biologically active derivatives of the reference molecules that have the desired activity, namely the ability to stimulate a cell-mediated immune response as defined above.

Generally, the term "analogue" refers to compounds having a native polypeptide sequence and structure having one or more additions, substitutions (generally conservative in terms of nature) and/or amino acid deletions, relative to the native molecule, to the extent that the modifications do not destroy the immunogenic activity. By the term "mutein", is meant the peptides having one or more elements imitating the peptide (peptoids), such as those described in the Patent Application PCT WO91/04282. Preferably, the analogue or the mutein have at least the same immunoactivity as the native molecule. Processes for preparing polypeptide analogues and muteins are known to a person skilled in the art and are described below.

The particularly preferred analogues include substitutions that are conservative in nature, i.e. the substitutions, which take place in a family of amino acids. Specifically, the amino acids are generally divided into 4 families, namely (1) the acid amino acids such as aspartate and glutamate, (2) the basic amino acids such as lysine, arginine and histidine, (3) the non-polar amino acids such as alanine, leucine, isoleucine, proline, phenylalanine, methionine and tryptophane and (4) the polar non-charged amino acids such as glycine, asparagine, glutamine, cysteine, serine, threonine and tyrosine. Phenylalanine, tryptophane and tyrosine are sometimes classified as aromatic amino acids. For example, it can reasonably be predicted that an isolated replacement of leucine by isoleucine or valine, of an aspartate by a glutamate, of a threonine by a serine, or a similar conservative replacement of one amino acid by another amino acid having a structural relationship, will not have a major effect on the biological activity. A person skilled in the art will easily determine the regions of the peptide molecule of interest that can tolerate a change by referring to the Hopp/Woods and Kyte-Doolittle plots, well known in the art.

By "homology", is meant the percentage of identity between two peptide molecules, such as polyproteins and polypeptides. Two amino acid sequences are "more or less homologous" to each other when the sequences have at least 60%, preferably at least 75%, more preferably also at least 80-85%, more preferably also at least 90% and still more preferably at least 95-98% or more of sequence identity over a defined length of the peptide molecules.

Generally, the term "identity" refers to an exact amino acid to amino acid correspondence of two peptide sequences. The percentage of identity can be determined by a direct comparison of the sequence information between two molecules by aligning the sequences, counting the exact number of mismatches between the two aligned sequences, dividing by the length of the shorter sequence and multiplying the result by 100. The percentage of identity can also be determined using computer programs such as ALIGN, Dayhoff, M. O. in Atlas of Protein Sequence and Structure M. O. Dayhoffed., 1981, 5 Suppl., 3: 482-489.

The nucleic acid and amino acid sequences of a certain number of HCV strains and isolates, and in particular of the protein NS3, of the protein NS4 and of the polypeptide NS5b, have already been determined.

For example, the isolate HCV-J1 is described in Okamoto H. et al., 1992, Nucleic Acids Res., 20: 6410-6410. The complete coding sequences of two independent HCV isolates, namely the isolates HCV-J and -BK, have been described in Kato et al., 1990, Proc. Natl. Acad., Sci., 87: 9524-9528 and in Takamizawa et al., 1991, J. Virol., 65: 1105-1113 respectively. As regards the isolate HCV-1, it is described in Choo et al., 1990, Brit. Med. Bull., 46: 423-441 and in Choo et al., 1991, op. cit. The isolate HVC-H has been described in Inchauspe G. et al, 1991, Proc. Natl. Acad. Sci., 88: 10292-10296. The isolate HCV-G9 has been described in Okamoto H., et al., 1994, J. Gen. Virol., 45: 629-635. The isolates HCV-J6 and -J8 have been described in Okamoto H., et al., 1991, J. Gen. Virol., 72: 2697-2704 and Okamoto H., et al., 1992, Virology, 188: 331-341 respectively. The isolate HVC-BEBE1 has been described in Nako H., et al., 1996, J. Gen. Virol., 141: 701-704 and the isolate HCV-NZL1 has been described in Sakamoto M., et al., 1994, J. Gen. Virol., 75: 1761-1768. As regards the isolate HCV-Tr, it has been described in Chayama K., et al., 1994, J. Gen. Virol., 75: 3623-3628. The isolates HCV-ED43 and -EUH1480 have been described in Chamberlain R. W., et al., 1997, J. Gen. Virol., 78: 1341-1347 and Chamberlain R. W., et al., 1997, Biochem. Biophys. Res. Commun., 236: 44-49 respectively. The isolate HCV-EUHK2 has been described in Adams A., et al., 1997, Biochem. Biophys. Res. Commun., 234: 393-396. The isolates HCV-VN235, -VN405 and -VN004 have been described in Tokita H., et al., 1998, J. Gen. Virol., 79: 1847. Finally, as regards the isolates HCV-JK049 and -JK046, they have been described in Tokita H. et al., 1996, J. Gen. Virol., 77: 293-301.

The HCV strains and isolates, as illustrated above, can have different genotypes, namely genotypes 1a (isolates HCV-1, -J1 and -H), 1b (isolates HCV-J and BK), 1c (isolate HCV-G9), 2a (isolate HCV-J6), 2b (isolate HCV-J8), 2c (isolate HCV-BEBE1), 3a (isolate HCV-NZL1), 3b (isolate HCV-Tr), 4a (isolate HCV-ED43), 5a (isolate HCV-EUH1480), 6a (isolate HCV-EUHK2), 7b (isolate HCV-VN235), 8b (isolate HCV-VN405), 9a (isolate HCV-VN004), 10a (isolate HCV-JK049) and 11a (isolate HCV-JK046).

According to one embodiment of the invention, NS3 and/or NS4 and/or NS5b originate from viruses of different genotypes.

According to another embodiment, NS3 and/or NS4 and/or NS5b originate from viruses of the same genotype, preferably of genotype 1b.

The polyprotein NS3/NS4 and the polypeptide NS5b contained in the peptide composition of the invention can be either of native origin, or of recombinant origin.

The polyprotein NS3/NS4 and the polypeptide NS5b of native origin are obtained from HCV strains or isolates, by means of the use of synthetic oligonucleotide primers that will serve to amplify the native viral sequences, either from sera of patients infected by the targeted viral genotype or genotypes, or from already purified viral RNA, originating for example from patients' blood or liver, or from complementary DNA that is free or cloned beforehand in an expression vector, or also from viral particles purified from biological samples or in vitro propagation system.

The polyprotein NS3/NS4 and the polypeptide NS5b of the invention of recombinant origin can also be obtained by the genetic engineering technique, which comprises the steps of:

culture of a microorganism or of eukaryotic cell(s) transformed using a nucleotide sequence coding for said polyprotein NS3/NS4 or for said polypeptide NS5b and recovery of the peptide produced by said microorganism or said eukaryotic cells.

This technique is well known to a person skilled in the art. For more details concerning this, reference can be made to the following work: Recombinant DNA Technology I, Editors Ales Prokop, Raskesh K Bajpai; Annals of the New-York Academy of Sciences, Volume 646, 1991.

The nucleotide sequences coding for the polyprotein NS3/NS4 and the polypeptide NS5b can be prepared by chemical synthesis in conjunction with a genetic engineering approach or by genetic engineering alone, using the techniques well known to a person skilled in the art and described for example in Sambrook J. et al., Molecular Cloning: A Laboratory Manual, 1989.

The nucleotide sequences coding for the polyprotein NS3/NS4 and the polypeptide NS5b can be inserted into expression vectors in a suitable expression system, in order to obtain the peptide composition of the invention.

Of course, the nucleotide sequences can be inserted into a single expression vector or into two different expression vectors. In the latter case, the sequence coding for the polyprotein NS3/NS4 is inserted into one of the two vectors and the sequence coding for the polypeptide NS5b is inserted into the other vector, these two vectors being either identical or different in nature.

Thus, another object of the invention is the expression vectors comprising a nucleotide sequence coding for the polyprotein NS3/NS4 and a nucleotide sequence coding for the polypeptide NS5b, as well as the means necessary to its expression.

By means necessary to the expression of a peptide is meant, the term peptide being used for any peptide molecule, such as protein, polyprotein, polypeptide, etc., any means that make it possible to obtain the peptide, such as in particular a promoter, a transcription terminator, a replication origin and preferably a selection marker.

The means necessary to the expression of a peptide are operationally linked to the nucleic acid sequence coding for the peptide of interest. By "operationally linked", is meant a juxtaposition of said elements necessary to the expression and of the gene coding for the peptide of interest, which are in a relationship such that it is possible for them to function in an expected manner. For example, additional bases can exist between the promoter and the gene of interest to the extent that their functional relationship is preserved.

The means necessary to the expression of a peptide can be homologous means, i.e. included in the genome of the vector used, or be heterologous. In the latter case, said means are cloned with the peptide of interest to be expressed.

Examples of heterologous promoters include (i) the viral promoters such as the SV40 promoter (simian virus 40), the promoter of the thymidine-kinase gene of the herpes simplex virus (TK-HSV-1), the LTR of the Rous sarcoma virus (RSV), the immediate first promoter of the cytomegalovirus (CMV) and the adenovirus major last promoter (MLP), as well as (ii) any cell promoter that controls the transcription of the genes coding for peptides in upper eukaryotes, such as the constitutive promoter of the diphosphoglycerate-kinase gene (PGK) (Adra et al., 1987, Gene, 60: 65-74), the promoter of the liver-specific alpha-1 antitrypsin and FIX genes and the SM22 promoter specific to the smooth muscle cells (Moessler et al., 1996, Development, 122: 2415-2425).

According to one embodiment of the invention, the nucleotide sequences coding for said polyprotein NS3/NS4 and said polypeptide NS5b originate from different genotypes.

According to another embodiment, the nucleotide sequences coding for said polyprotein and said polypeptide originate from a virus of the same genotype, preferably genotype 1b.

Here too, by "nucleotide sequence" is meant all the sequences coding for the native polyprotein NS3/NS4 and the native polypeptide NS5b, as well as for their analogues, muteins and homologues, as defined previously.

Said sequences contained in the expression vector can be directly interlinked under the control of a single promoter and/or of a single expression-regulating element, or they can be separate, each being dependent on expression promoters and/or regulators that are independent identical or different.

As expression vectors that are suitable for the purposes of the invention, there can be mentioned for example plasmids, adenovirus-type viral vectors, poxviruses, vaccinia viruses, baculoviruses, *salmonella*-type bacterial vectors, BCG.

Adenoviruses have been detected in numerous animal species, do not integrate and are only slightly pathogenic. They are capable of infecting a variety of cell types, cells in division and cells at rest. They possess a natural tropism for the bronchial epithelia. Moreover, they have been used as live enteric vaccines for many years with an excellent safety profile. Finally, they can easily be made to grow and be purified in large amounts. These characteristics have meant that the adenoviruses are particularly appropriate for use as expression vectors and in particular as gene therapy vectors for therapeutic purposes and for vaccines.

According to a preferred embodiment, the vector of the invention is an adenovirus.

Examples of adenoviruses to be used in the present invention can be derived from any source of human or animal origin, in particular of canine origin (for example CAV-1 or CAV-2; reference Genbank CAV1GENOM and CAV77082 respectively), of avian origin (reference Genbank AAVEDS-DNA), of bovine origin (such as BAV3, Seshidhar Reddy et al., 1998, J. Virol., 72: 1394-1402), of ovine, feline, porcine origin, of simian origin, or from one of their hybrids. Any serotype can be used. However, adenoviruses of human origin are preferred and in particular adenovirus 5 (AdIV).

Generally, the mentioned viruses are available from the ATCC collections and have been the subject of numerous publications describing their sequence, their organization and their biology, which allows a person skilled in the art to use them easily. For example, the sequence of the adenovirus type 5 is described in the Genbank database (M73260 and M29978) and is incorporated here by way of reference.

The genome of the adenovirus is constituted by a double-strand linear DNA molecule of approximately 36 kb carrying more than approximately 30 genes necessary for terminating the viral cycle. The first genes are divided into 4 regions dispersed in the genome of the adenovirus (E1 to E4). The E1, E2 and E4 regions are essential for viral replication. The E3 region is considered as a non-essential region on the basis of the observation that mutant viruses appear naturally or the hybrid viruses having lost this E3 region continue to replicate like wild-type viruses in cultured cells (Kelly and Lewis, 1973, J. Virol., 12: 643-652). The last genes (L1 to L5) mostly code for the structural proteins constituting the viral capsid. They overlap at least in part the first transcription units and are transcribed from a single promoter (MLP for Major Late Promoter). Moreover, the adenoviral genome carries at the two ends of the cis-acting regions essential for DNA replication, the 5' and 3' inverted terminal repeats (ITRs) and a packing sequence respectively.

The adenoviruses currently used in gene therapy protocols are stripped of the majority of the E1 region, which renders the viruses deficient at the level of their replication in order to avoid their dissemination in the environment and in the host organism. Moreover, most of the adenoviruses are also stripped of the E3 region in order to increase their cloning capacity. The feasibility of gene transfer using these vectors has been demonstrated in a variety of tissues in vivo (see for example Yei et al., 1994, Hum. Gene Ther., 5: 731-744; Dai et al., 1995, Proc. Natl. Acad Sci. USA, 92: 1401-1405; U.S. Pat. No. 6,099,831; and U.S. Pat. No. 6,013,638).

Preferably, the promoters used in the adenoviruses as expression vectors are heterologous promoters such as the CMV and SV40 promoters.

Preferably also, the CMV promoter is the promoter of the polyprotein NS3/NS4 and the expression vector comprises as nucleotide sequence coding for said polyprotein the expression cassette CMV-NS3-NS4.

By "expression cassette", is meant a DNA sequence containing a promoter and an open reading frame for the expression of the peptide of interest, to be inserted into a vector.

Preferably also, the SV40 promoter is the promoter of the polypeptide NS5b and the expression vector comprises as nucleotide sequence coding for said polypeptide the expression cassette SV40-NS5b.

According to one embodiment of the invention, the genome of the adenovirus is modified so as to replace the E1 region by the expression cassette CMV-NS3-NS4 and to replace the E3 region by the expression cassette SV40-NS5b.

The methods of suppression and of insertion of DNA sequences into expression vectors are widely known to a person skilled in the art and consist in particular of steps of enzymatic digestion and ligation.

Another expression vector particularly appropriate for the purposes of the invention is a poxvirus, which constitutes another embodiment of the invention.

The poxviruses constitute a group of enveloped complex viruses, differing principally in their unusual morphology, their large DNA genome and their cytoplasmic replication site. The genome of several elements of the poxviridae, comprising the Copenhagen strain of the vaccinia virus (VV) (Goebel et al., 1990, Virol. 179: 247-266 and 517-563) and the modified vaccinia virus Ankara (MVA) strain (Antoine et al., 1998, Virol., 244: 635-396), has been mapped and sequenced. The VV strain possesses a double-strand DNA genome of approximately 192 kb coding for approximately 200 proteins approximately 100 of which are involved in the assembly of the virus. The MVA strain is a highly attenuated strain of vaccinia virus, generated by more than 500 passages in series of the vaccinia virus Ankara strain (CVA) over chicken embryo fibroblasts (Mayr et al., 1975, Infection, 3: 6-16). The MVA virus has been deposited in the Collection Nationale de Cultures de Microorganismes (CNCM) under Number I-721. The determination of the complete sequence of the MVA genome and comparison with that of the VV allows precise identification of the alterations that have appeared in the viral genome and the definition of seven deletions (I to VII) and of numerous mutations leading to fragmented open reading frames (Antoine et al., 1998, Virology, 244: 365-396).

Other examples of poxviruses that are appropriate for the purposes of the invention include duck pox, fowl pox, cow pox, entomopox, monkey pox, swine pox and penguin pox.

The poxvirus is found in two morphologically distinct forms, called intracellular mature virus (IMV) and enveloped extracellular virus (EEV).

The poxvirus used as an expression vector of the invention has at least one of the following characteristics, taken alone or in combination:
  (i) the poxvirus is an MVA virus,
  (ii) the poxvirus is in the IMV morphological form, and
  (iii) the genome of the poxvirus is modified so as to insert the expression cassette NS3/NS4 and to insert the expression cassette NS5b.

When the genome of the poxvirus is modified so as to insert the two cassettes of interest, the means necessary to their expression are homologues. Thus, in the case where the MVA virus is used, the expression of NS3/NS4 can be for example under the control of the promoter ph5r so that the corresponding expression cassette is ph5r-NS3-NS4, and the expression of NS5b can be for example under the control of the promoter p7.5 so that the corresponding expression cassette is p7.5-NS5b, and vice versa.

According to a particular embodiment, when the genome of the poxvirus is modified so as to insert the two cassettes of interest, the two said expression cassettes are oriented in the same direction.

According to another particular embodiment, they are oriented in the opposite direction.

Here too, the expression cassettes are inserted into the genome of the poxvirus in a manner known to a person skilled in the art, as indicated previously.

The vectors of the invention can also comprise sequences necessary for targeting peptides towards particular cell compartments. An example of targeting can be the targeting towards the endoplasmic reticulum obtained using address sequences of the leader sequence type originating from the protein E3 of the adenovirus (Ciernik I. F., et al., The Journal of Immunology, 1999, 162, 3915-3925).

They can also comprise sequences necessary for targeting towards the dendritic cells and for targeting at the membrane of the cells.

An object of the invention is also the microorganisms and the eukaryotic cells transformed by an expression vector of the invention.

By way of examples of microorganism that are suitable for the purposes of the invention, there can be mentioned the yeasts, such as those of the following families: *Saccharomyces, Schizosaccharomyces, Kluveromyces, Pichia, Hanseluna, Yarrowia, Schwantomyces, Zygosaccharomyces, Saccharomyces cerevisiae, Saccharomyces carlsbergensis* and *Kluveromyces lactis* being preferred; and the bacteria, such as *E. coli* and those of the following families: *Lactobacillus, Lactococcus, Salmonella, Streptococcus, Bacillus* and *Streptomyces*.

By way of examples of eukaryotic cells, there can be mentioned cells originating from animals such as mammals, reptiles, insects and equivalent. The preferred eukaryotic cells are cells originating from the Chinese hamster (CHO cells), monkey (COS and Vero cells), baby hamster kidney (BHK cells), pig kidney (PK 15 cells) and rabbit kidney (RK13 cells), human osteosarcoma cell lines (143 B), HeLa human cell lines and the human hepatoma cell lines (Hep G2-type cells), as well as insect cell lines (for example of *Spodoptera frugiperda*).

The host cells can be provided in cultures in suspension or in flasks, in tissue cultures, organ cultures and equivalent. The host cells can also be transgenic animals.

The invention also relates to antibodies directed against one of the peptide compositions of the invention as defined previously or against one of the expression vectors of the invention as defined previously.

The antibodies according to the invention are either polyclonal or monoclonal antibodies.

The abovementioned polyclonal antibodies can be obtained by immunization of an animal with the peptide composition of the invention or with the vector of the invention as "antigen of interest", followed by the recovery of the antibodies sought in purified form, by sampling the serum of said animal, and separation of said antibodies from the other constituents of the serum, in particular by affinity chromatography on a column to which is fixed an antigen specifically recognized by the antibodies, in particular a viral antigen of interest.

The monoclonal antibodies can be obtained by the hybridomas technique the general principle of which is recalled hereafter.

In a first step, an animal, generally a mouse, (or cells in culture within the framework of in vitro immunizations) is immunized with the peptide composition of the invention or with the vector of the invention as "antigen of interest", the B lymphocytes of which are then capable of producing antibodies against said antigen. These antibody-producing lymphocytes are then fused with "immortal" myelomatous cells (murine in the example) in order to produce hybridomas. From the thus-obtained heterogeneous mixture of cells, a selection is then made of cells capable of producing a particular antibody and multiplying indefinitely. Each hybridoma is multiplied in clone form, each leading to the production of a monoclonal antibody the recognition properties of which vis-à-vis the antigen of interest can be tested for example by ELISA, by immunotransfer in one or two dimensions, by immunofluorescence, or using a biocaptor. The monoclonal antibodies thus selected are subsequently purified in particular according to the affinity chromatography technique described above.

The peptide compositions, the expression vectors, the nucleotide sequences coding for said polyprotein NS3/NS4 and said polypeptide NS5b, as well as the antibodies of the invention are particularly effective for the inhibition, prevention and control of the infection of patients carrying the HCV virus, so that their use for the preparation of a medicament constitutes another object of the invention.

The present invention also relates to a pharmaceutical composition, in particular a vaccine, containing as active ingredient the peptide composition of the invention, or an expression vector of the invention, or an expression vector comprising a nucleotide sequence coding for the polyprotein NS3/NS4 with an expression vector comprising a nucleotide sequence coding for the polypeptide NS5b, or the nucleotide sequences coding for said polyprotein NS3/NS4 and said polypeptide NS5b, said nucleotide sequences corresponding to the sequences contained in the expression vectors of the invention, placed under the control of elements necessary to an expression constitutive of and/or inducible from said peptides, or at least one of the antibodies of the invention.

By elements necessary to an expression constitutive of the peptides, is meant a promoter that is ubiquitous or specific to the eukaryotic cells.

As elements necessary to an expression inducible from the peptides, there can be mentioned the elements of regulation of the operon of *E. coli* for tetracycline resistance (Gossen M. et al., Proc Natl Acad Sci USA, 89: 5547-5551 (1992).

According to a particular embodiment of the invention, the pharmaceutical composition also contains a pharmaceutically appropriate vehicle. Of course, a person skilled in the art will easily determine the nature of the pharmaceutically appropriate vehicle and the quantity of polypeptides to be used as a function of the constituents of the pharmaceutical composition.

The quantity and nature of the pharmaceutically appropriate vehicle can be easily determined by a person skilled in the art. They are chosen according to the desired pharmaceutical form and method of administration.

The pharmaceutical compositions of the invention are appropriate for oral, sublingual, sub-cutaneous, intramuscular, intravenous, topical, local, intratracheal, intranasal, transdermal, rectal, intraocular, intra-auricular administration, said active ingredient being able to be administrated in a unitary dosage form of administration.

The unitary dosage forms of administration can be for example tablets, gelatin capsules, granules, powders, solutions or injectable oral suspensions, transdermal patches, forms of sublingual, buccal, intratracheal, intraocular, intranasal, intra-auricular or by inhalation administration, forms of topical, transdermal, sub-cutaneous, intramuscular or intravenous administration, forms of rectal administration, or implants. For topical administration, creams, gels, ointments, lotions or collyriums can be envisaged.

These galenic forms are prepared according to the usual methods of the fields considered.

Said unitary dosage forms are dosed in order to allow daily administration of 0.001 to 10 mg of active ingredient per kg of body weight, according to the galenic form.

There may be particular cases where higher or weaker dosages are appropriate; the scope of the invention is not exceeded by such dosages. According to usual practice, the dosage appropriate to each patient is determined by the doctor according to the method of administration, the weight and the response of the patient.

According to another embodiment of the invention, the present invention also relates to a method of treatment of the pathologies associated with the hepatitis C virus, which comprises the administration, to a patient, of an effective dose of a medicament of the invention.

The pharmaceutical compositions of the invention preferably contain as active ingredient one of the vectors of the invention or an expression vector comprising a nucleotide sequence coding for the polyprotein NS3/NS4 with an expression vector comprising a nucleotide sequence coding for the polypeptide NS5b, so that they are useful in prophylactic and therapeutic vaccination.

Prophylactic and therapeutic vaccination can be implemented by injection of a vaccine based on one or more expression vectors of the invention, to the extent that the expression vector or vectors finally code for the polyprotein NS3/NS4 and for the polypeptide NS5b as active ingredient, said injection being or being not followed by boosters. It can also be implemented by injecting two different types of expression vectors of the invention, firstly an adenovirus, then a poxvirus, simultaneously or at different times, and vice versa.

These vectors can be contained in a pharmaceutical kit.

Also, another object of the invention is pharmaceutical kits, in particular vaccinal, comprising at least one expression vector comprising a nucleotide sequence coding for the polyprotein NS3/NS4 and at least one expression vector comprising a nucleotide sequence coding for the polypeptide NS5b.

Another object of the invention is pharmaceutical kits, in particular vaccinal, comprising at least one expression vector of adenovirus type as defined previously and/or at least one expression vector of poxvirus type as defined previously.

Prophylactic and therapeutic vaccination can also be implemented by injection of a vaccine based on at least one expression vector of the invention, or an expression vector comprising a nucleotide sequence coding for the polyprotein NS3/NS4 with an expression vector comprising a nucleotide sequence coding for the polypeptide NS5b, and at least one pharmaceutical composition of the invention constituted by the peptide composition of the invention or the antibodies of the invention. It can also be implemented by injection of a vaccine based on at least one expression vector of the invention, or an expression vector comprising a nucleotide sequence coding for the polyprotein NS3/NS4 with an expression vector comprising a nucleotide sequence coding for the polypeptide NS5b, and at least one nucleotide sequence coding for the polyprotein NS3/NS4 and for the polypeptide NS5b.

Also, another object of the invention is pharmaceutical kits, in particular vaccinal, comprising at least one expression vector of the invention, or an expression vector comprising a nucleotide sequence coding for the polyprotein NS3/NS4 with an expression vector comprising a nucleotide sequence coding for the polypeptide NS5b, and at least one pharmaceutical composition of the invention or at least one nucleotide sequence coding for the polyprotein NS3/NS4 and for the polypeptide NS5b.

Figure 1A:
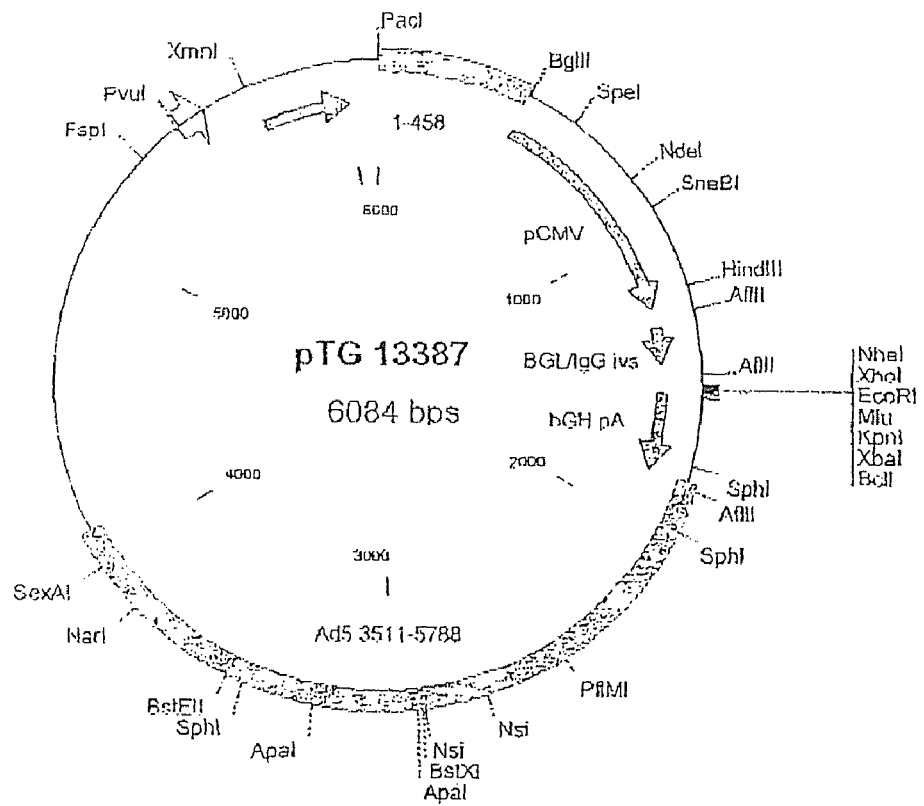
Figure 1B:
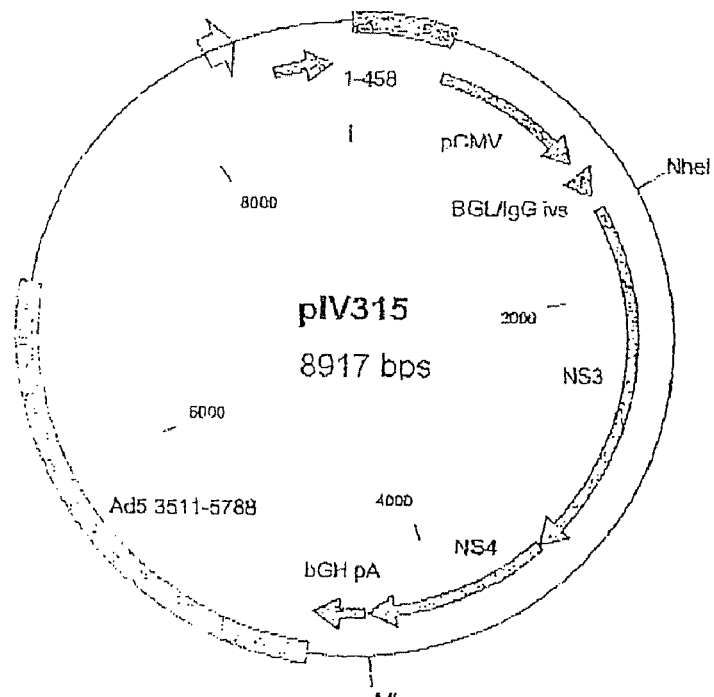
Figure 1C:
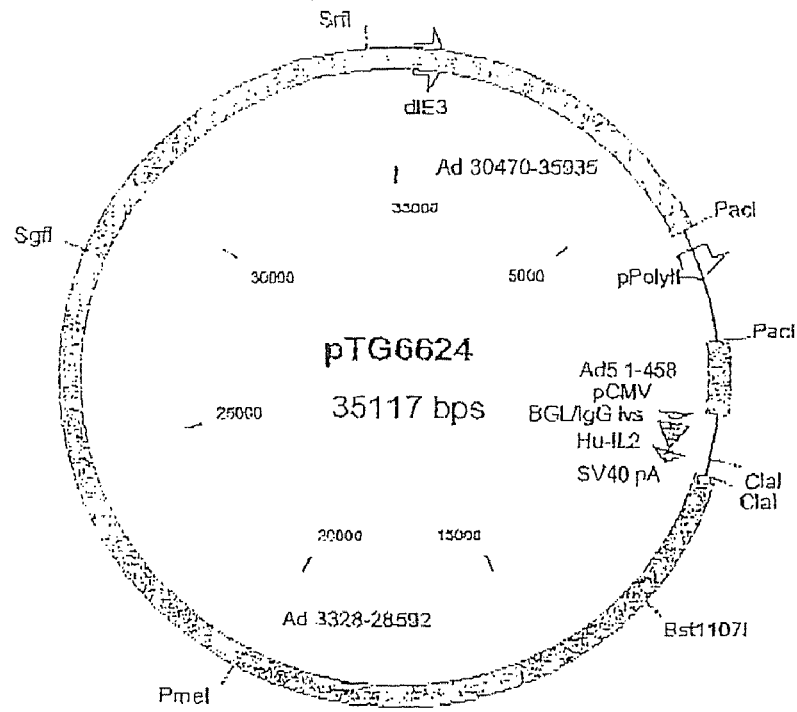
Figure 1D:
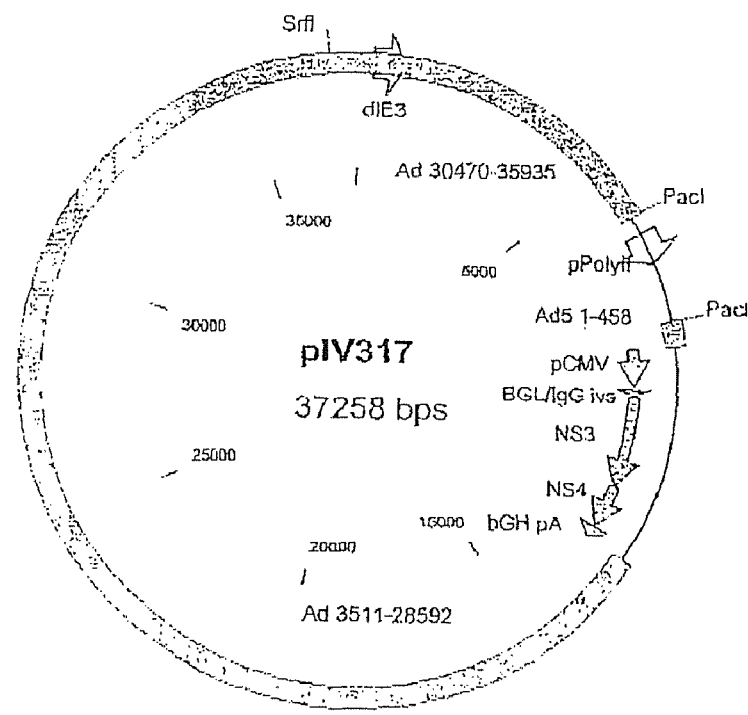
Figure 1E:
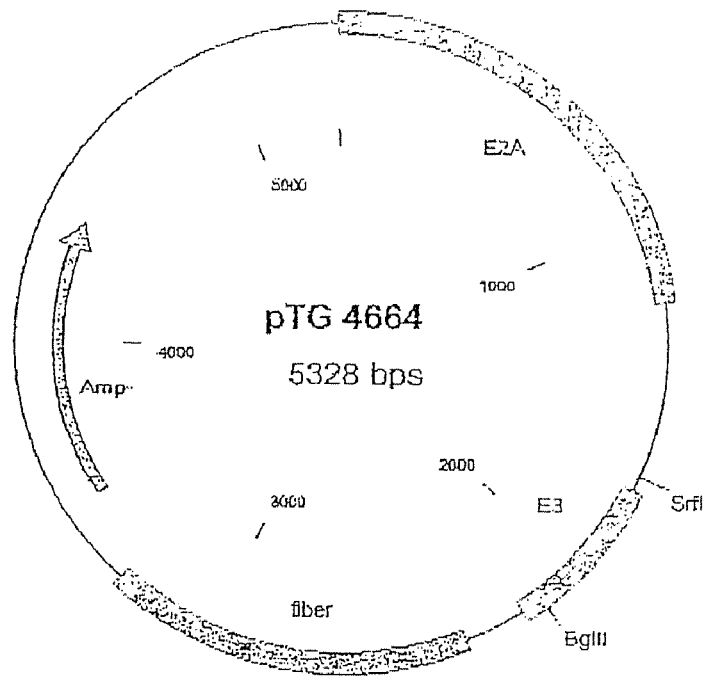
Figure 1F:
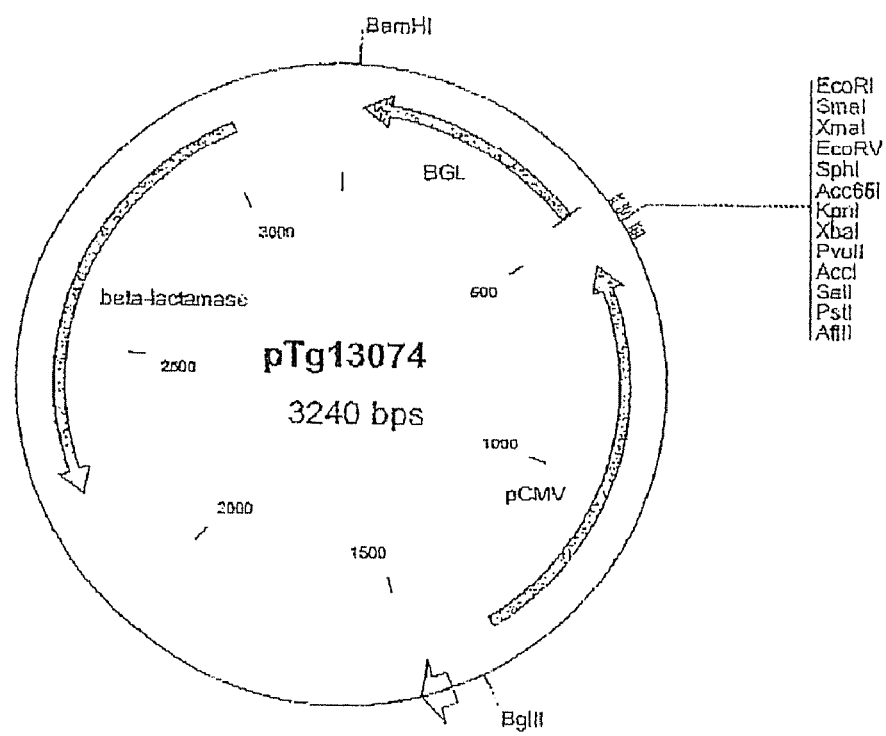
Figure 1G:
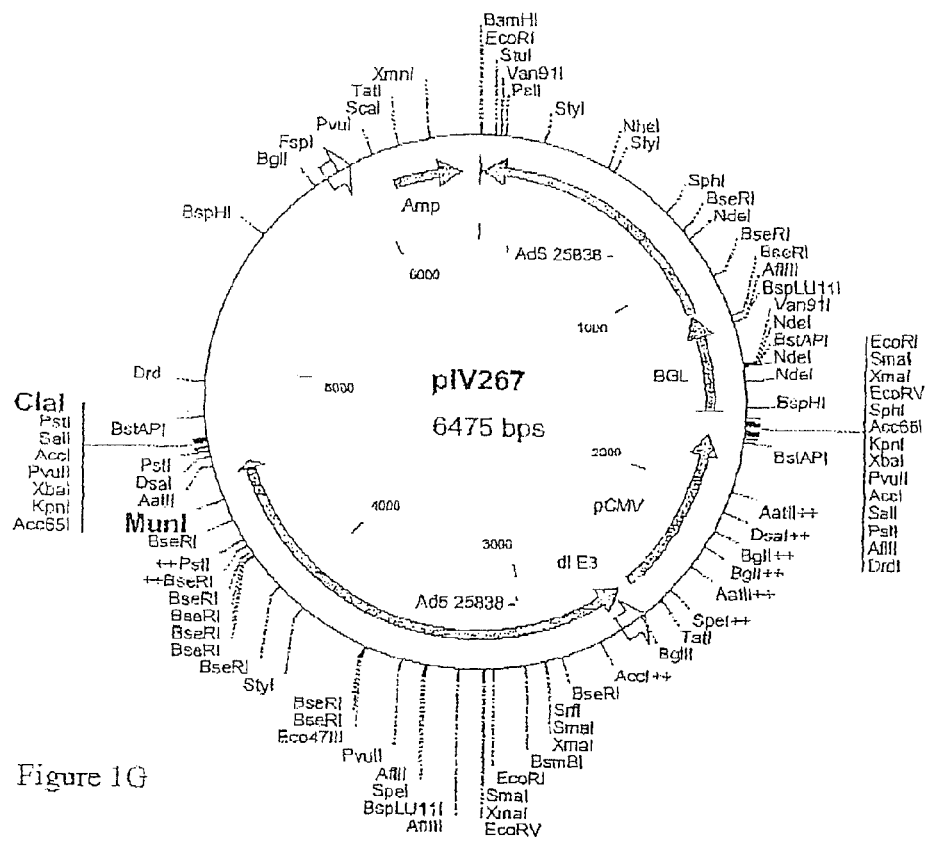
Figure 1H:
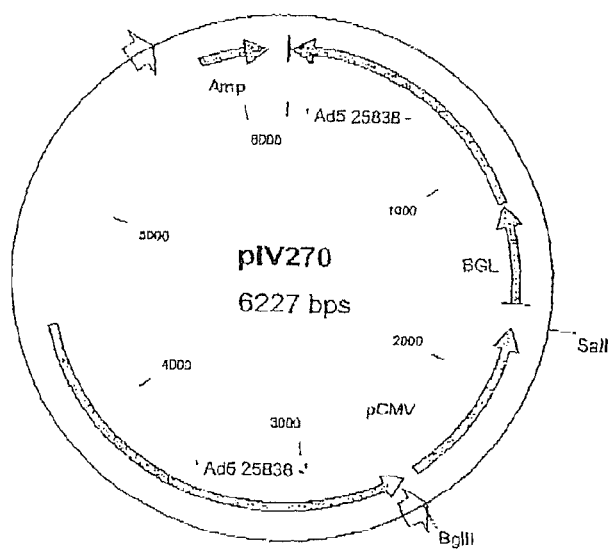
Figure 1I:
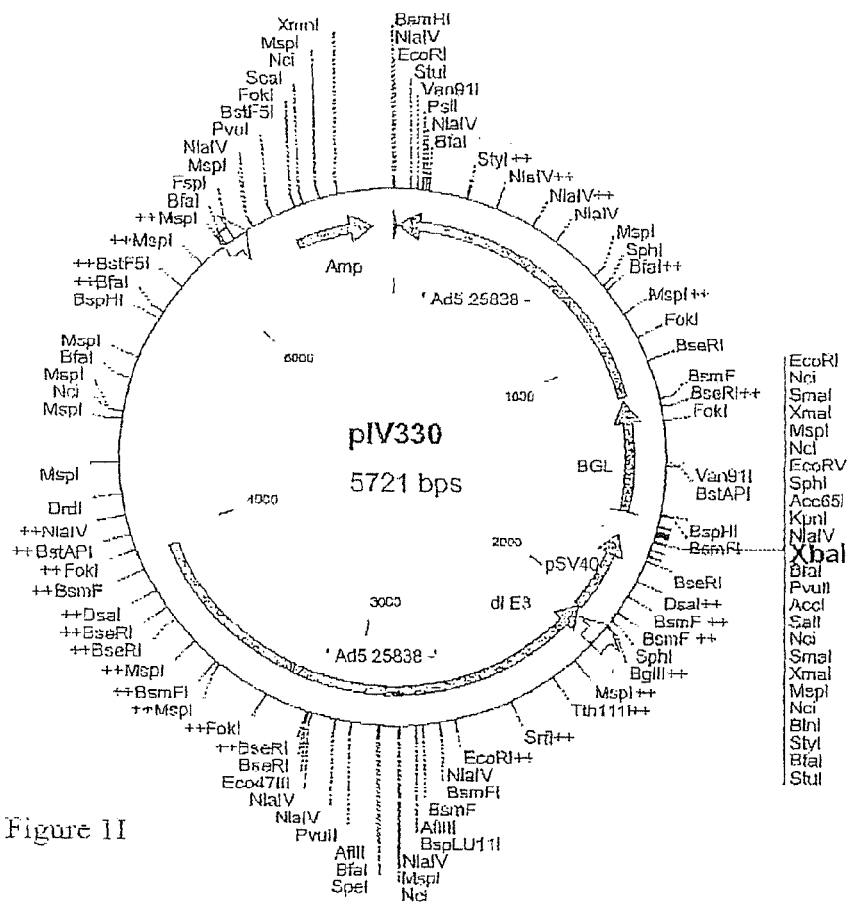
Figure 1J:
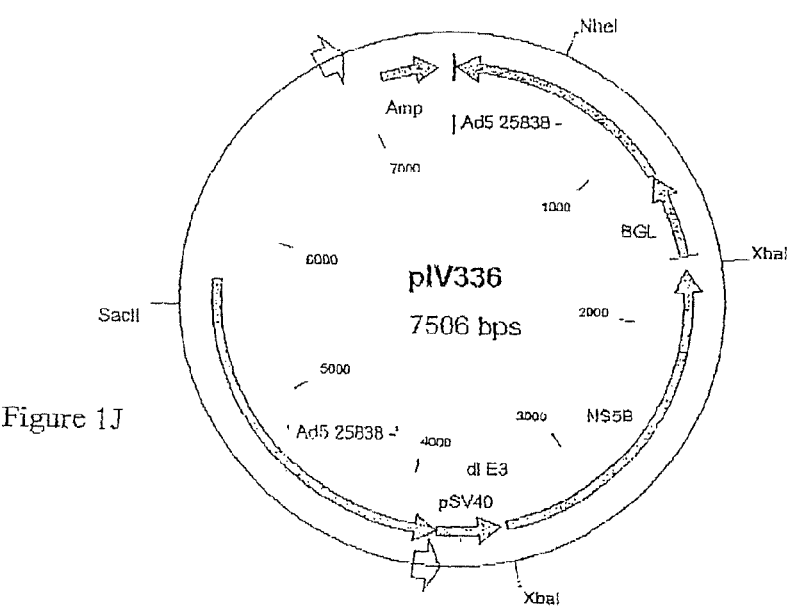
Figure 1K:
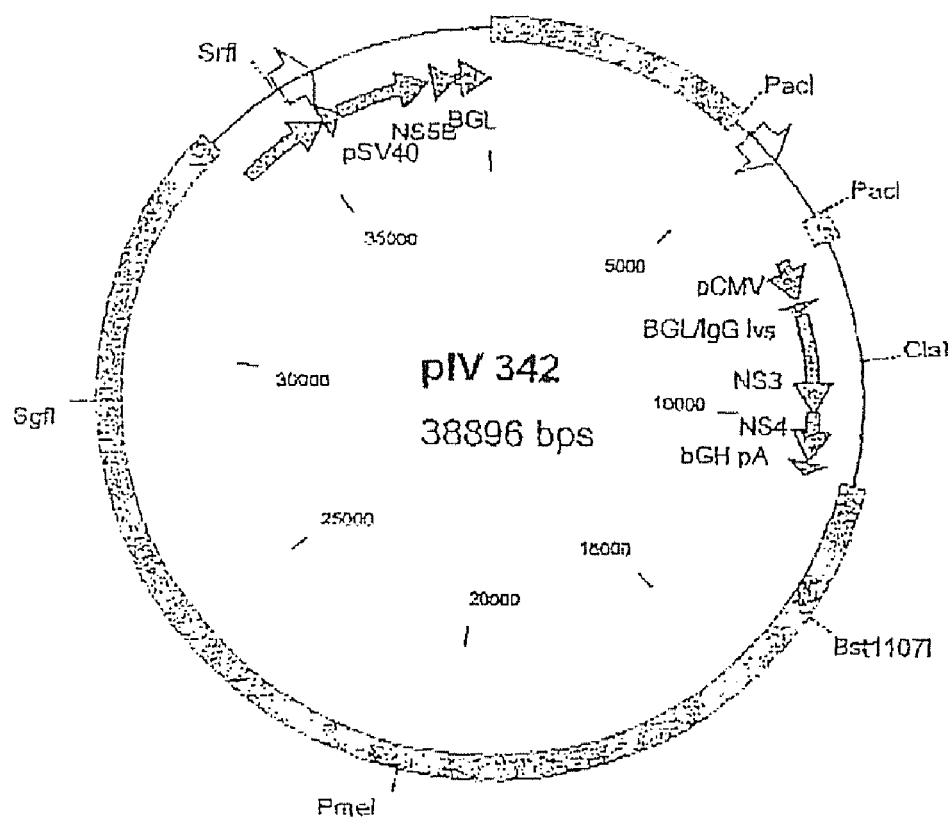
Figure 2B:
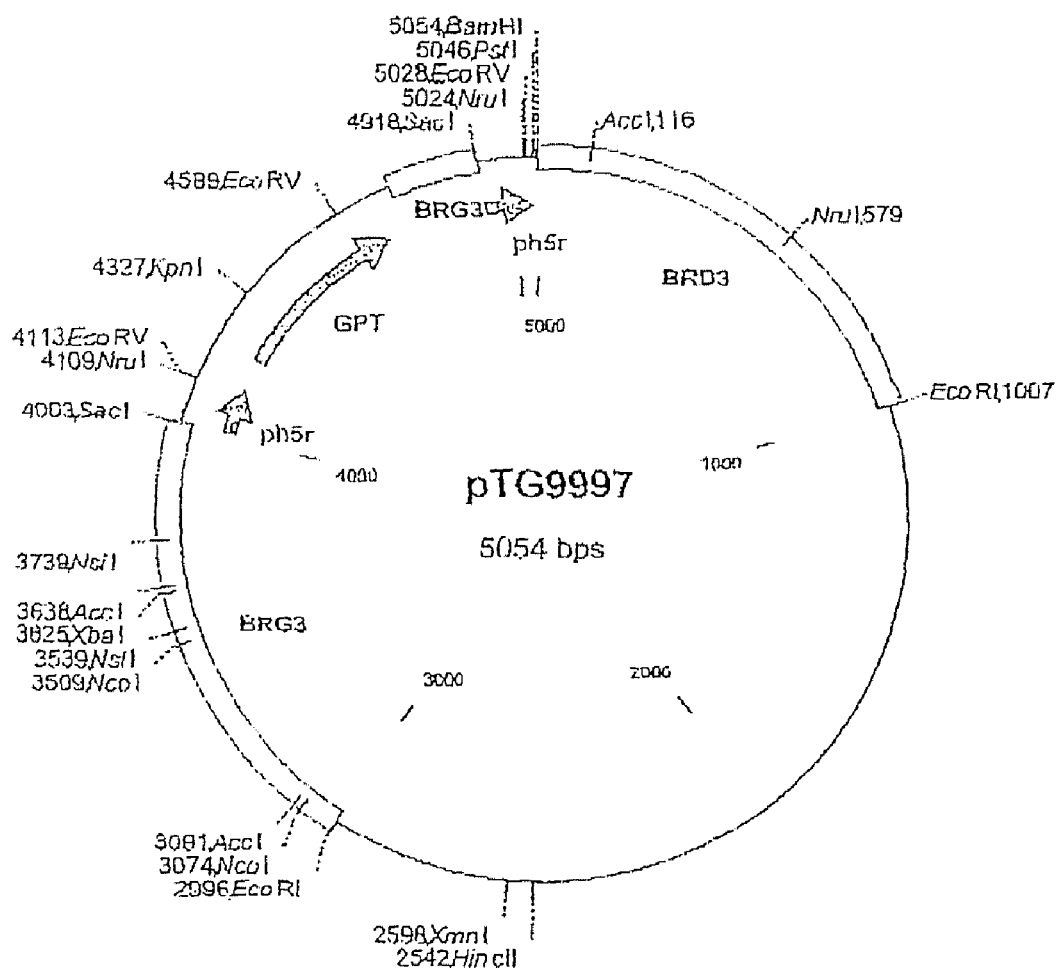
Figure 2C:
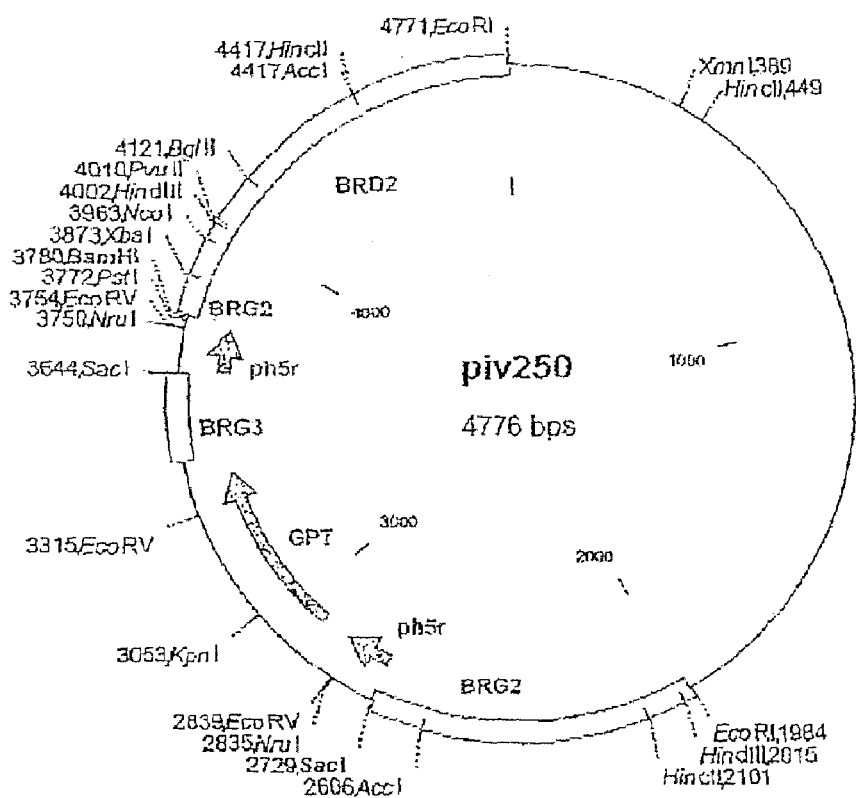
Figure 2D:
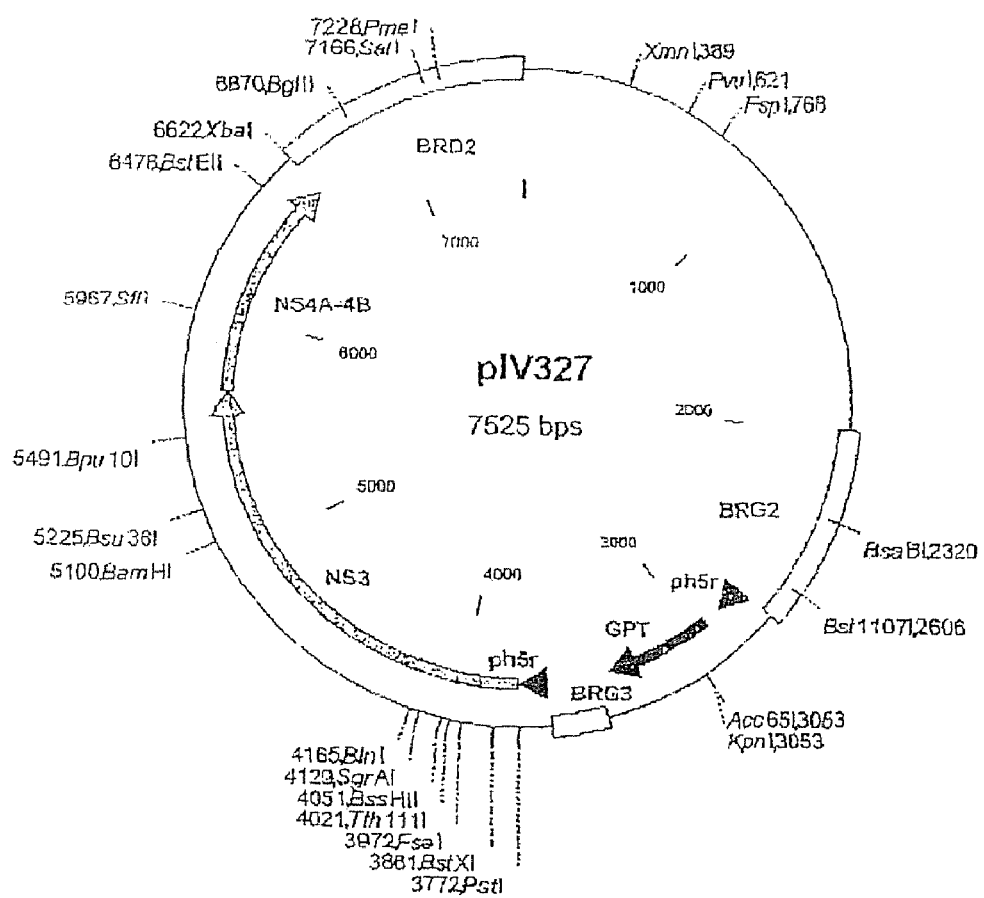
Figure 2E:
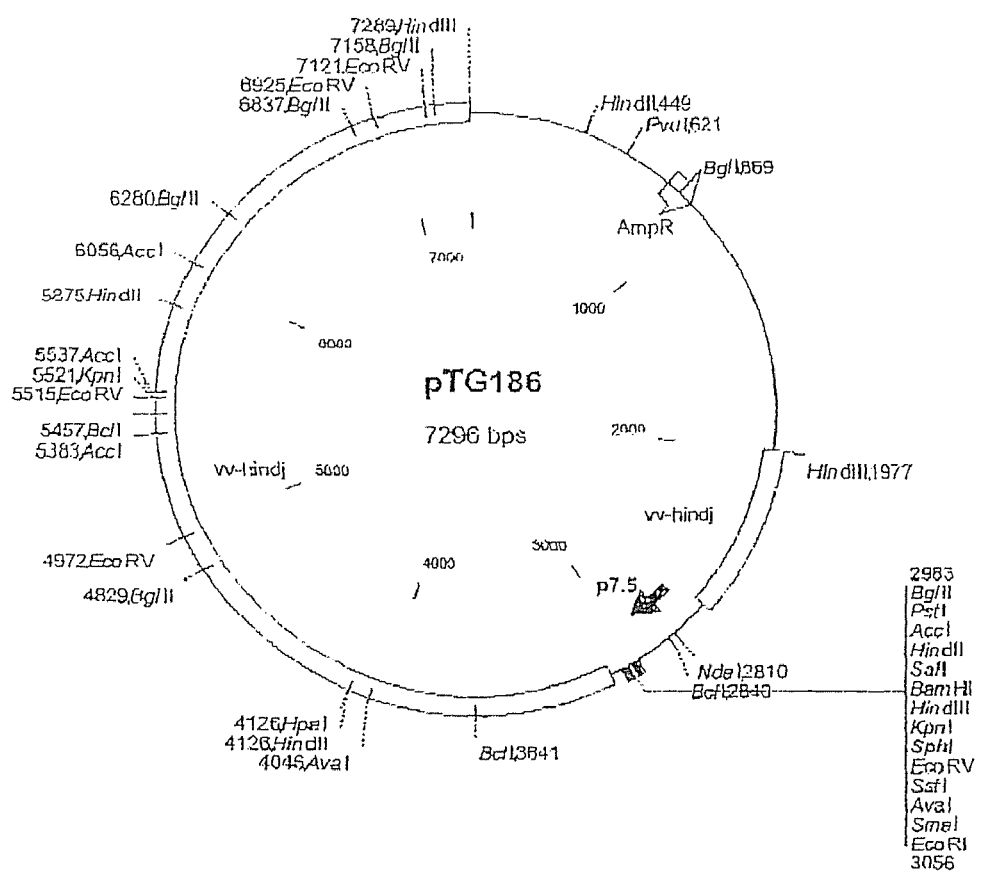
Figure 2F:
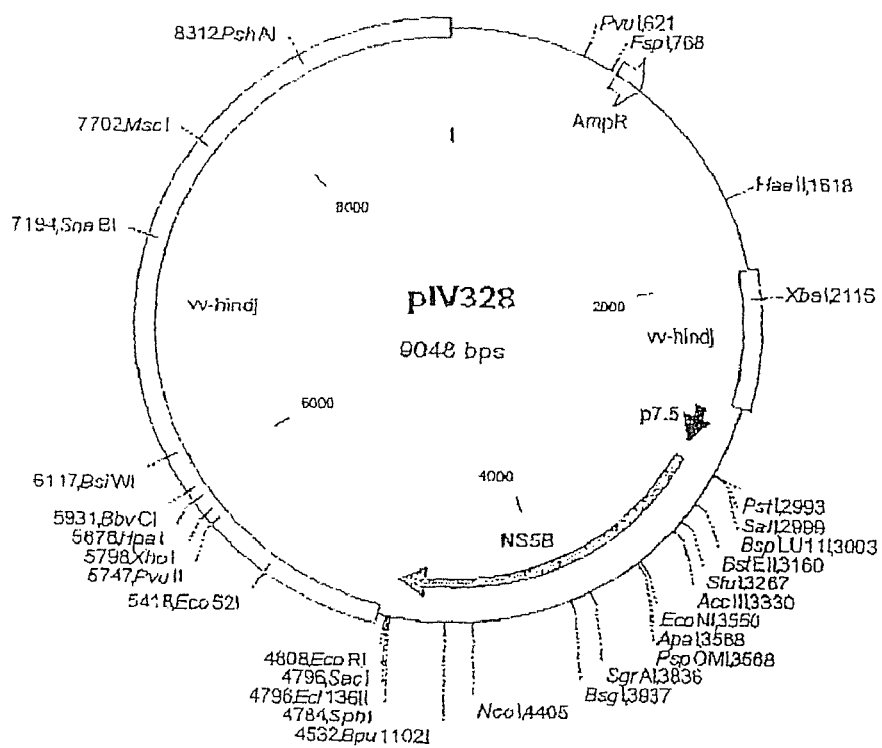
Figure 2G:
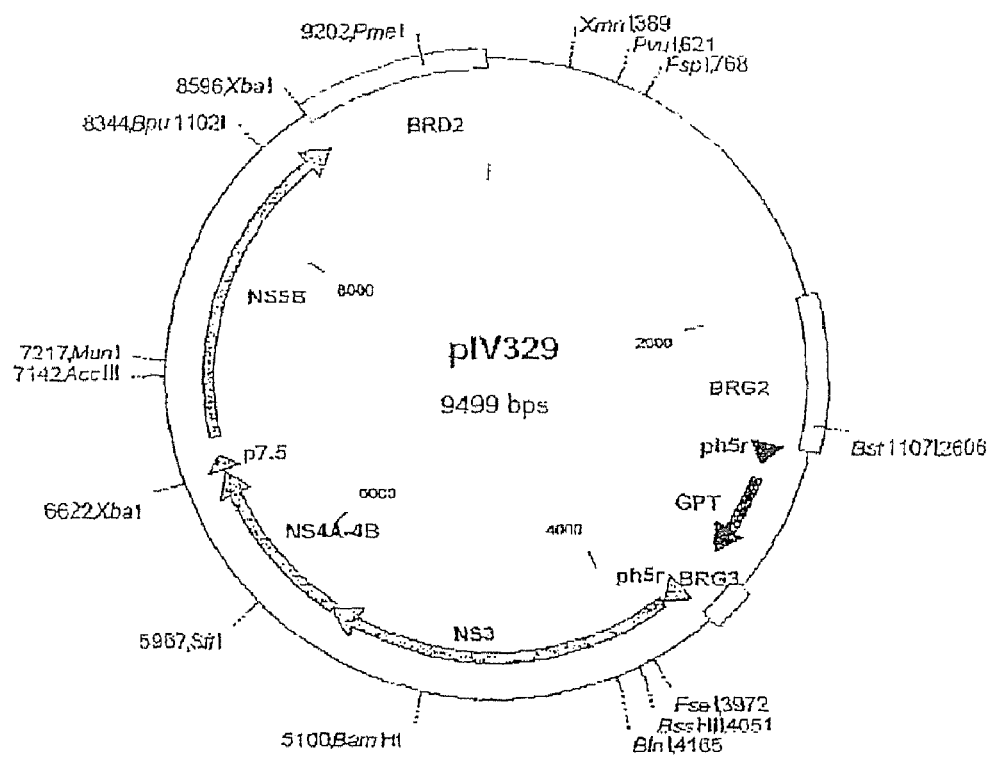
Figure 2H:
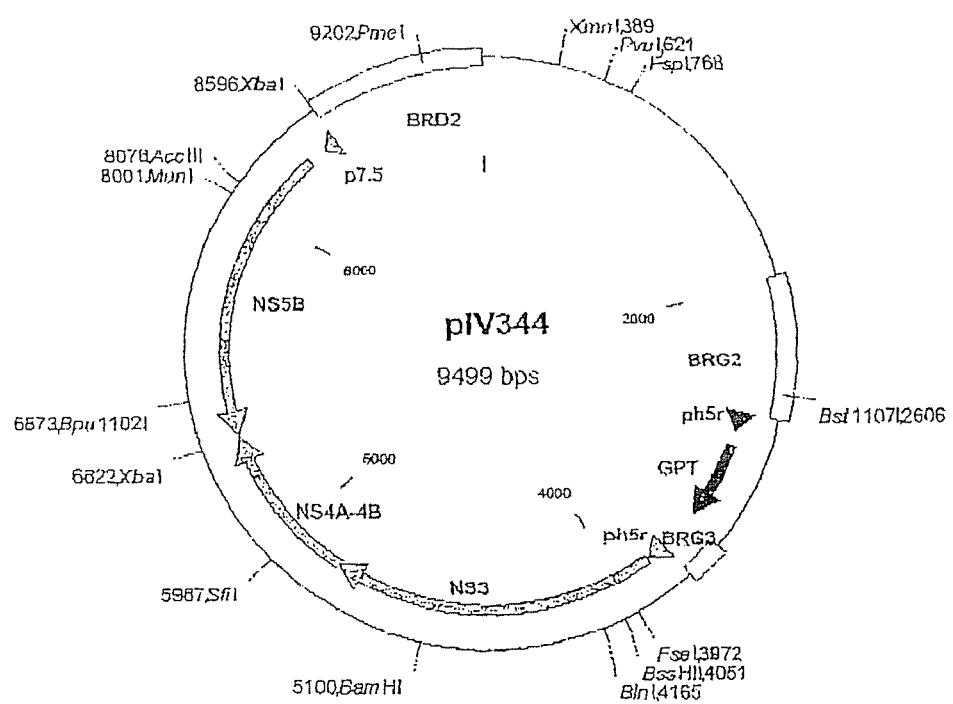
Figures 3, 3A:
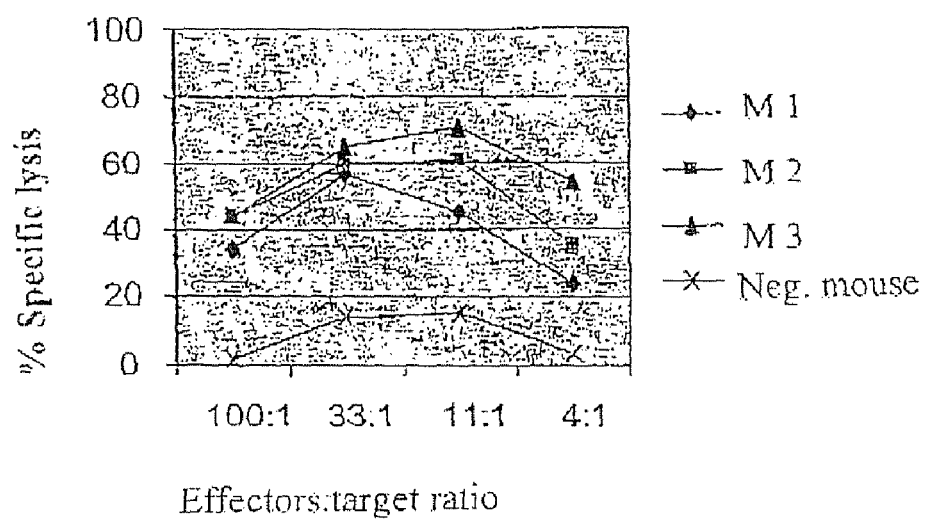
Figure 3B:
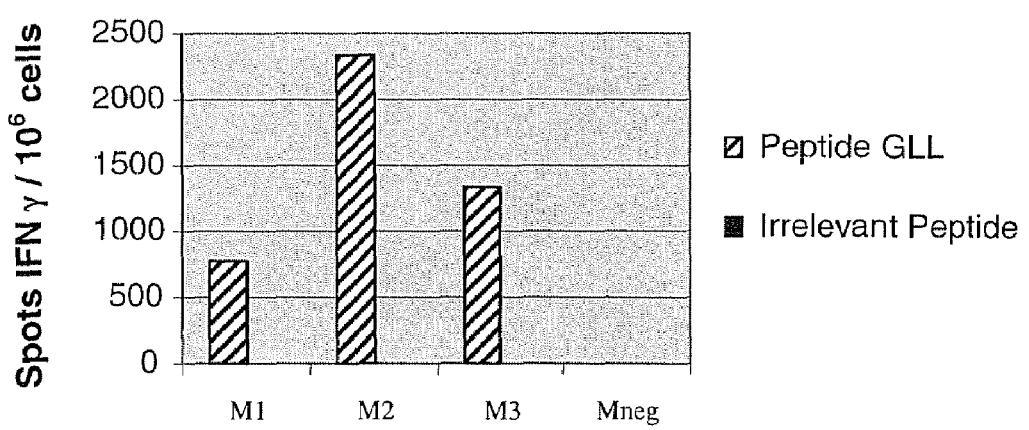
Figure 4:
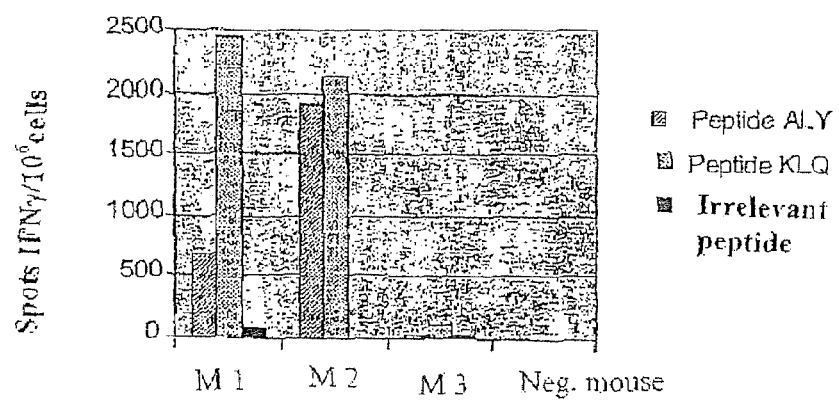
Figure 5:
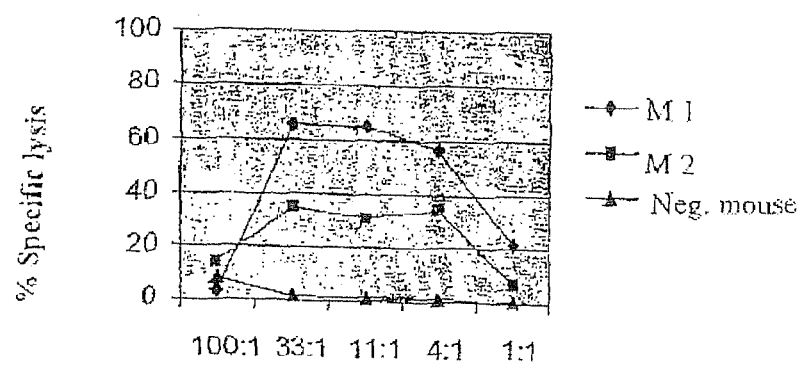
Figure 6:
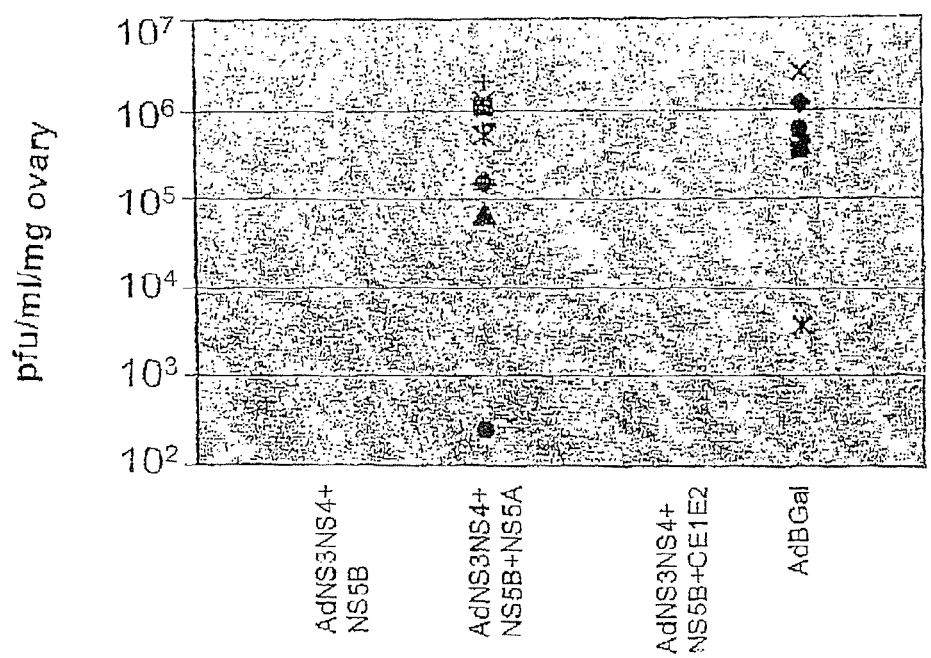
Figure 7:
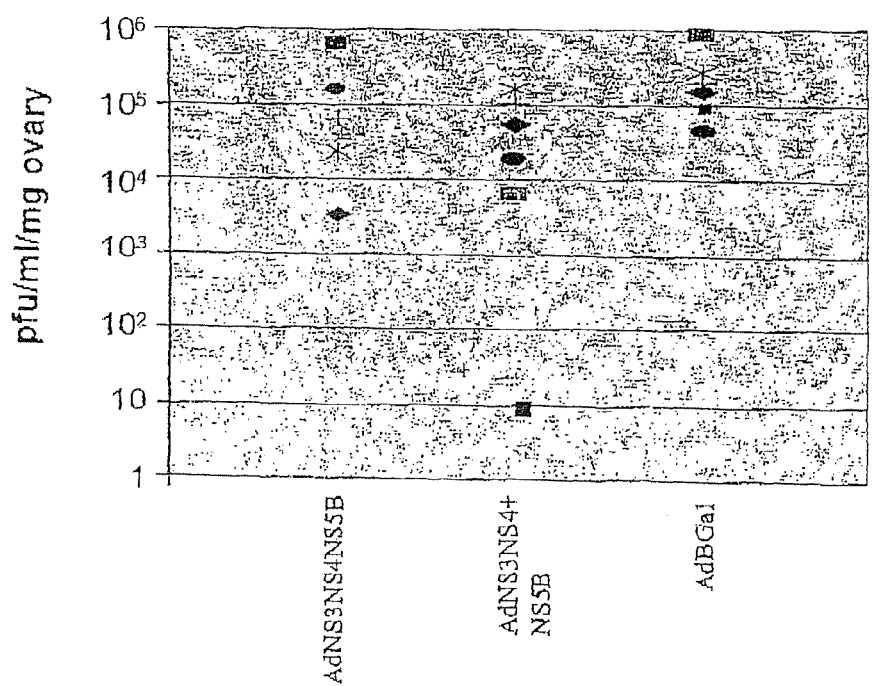

The present invention will be better understood using the following examples that are given only by way of illustration, and are non-limitative, as well as using the attached FIGS. 1 to 7, in which:

FIG. 1A to 1K represents the maps of the different plasmids used for obtaining an adenovirus AdNS3NS4NS5b according to the invention, on which are indicated the sites of the different restriction enzymes and the location of the sequence fragments coding for NS3/NS4 and for NS5b, FIG. 2A to 2H represents the maps of the different plasmids used for obtaining a poxvirus MAV NS3NS4NS5b according to the invention, on which are indicated the sites of the different restriction enzymes and the location of the sequence fragments coding for NS3/NS4 and pour NS5b, FIG. 3 gives the cell response induced by the adenovirus AdNS3NS4, either according to the CTL test (FIG. 3A) where the epitope GLL was used for stimulating the splenocytes in culture and for loading the CTL targets and the result of which is expressed as a specific lysis percentage as a function of the effector/target ratio, or according to the ELISPOT test (FIG. 3B), specific to the epitope GLL, where the result is given in numbers of spots/$10^6$ cells, FIG. 4 gives the cell response induced by the adenovirus AdNS5b according to the test ELISPOT, specific to the epitopes ALY and KLP, FIG. 5 gives the cell response induced by the adenoviris AdCEIE2 according to the CTL test where the epitope DLM was used for stimulating the splenocytes in culture and for loading the targets of the CTL and the result of which is expressed as a specific lysis percentage as a function of the effector/target ratio, FIG. 6 gives the titre of the recombinant vaccinia virus, resulting from the trial test, in pfu/ml/mg ovary, for the 4 groups of 8 mice immunized by the different combinations of adenovirus: AdNS3NS4+AdNS5b (1st group), the adenoviruses AdNS3NS4+AdNS5b+AdNS5a (2nd group), the adenoviruses AdNS3NS4+AdNS5b+AdCEIE2 (3rd group) and the adenovirus AdβGal (4th group) and FIG. 7 gives the titre of the recombinant vaccinia virus, resulting from the trial test, in pfu/ml/mg ovary, for the 3 groups of 8 mice immunized by the following different combinations of adenovirus: AdNS3NS4NS5b (1st group), AdNS3NS4+AdNS5b (2nd group) and AdβGal (3rd group).

EXAMPLE 1

Preparation of an Adenovirus Allowing the Expression of the Proteins NS3/NS4 and NS5b According to the Invention 1. Adenovirus The recombinant adenoviruses are generated by transfection (CaPO3) of the complementation line 293 (Graham, Smiley, et al. 1977) after linearization of the genomes by PacI. The recombinant viruses propagate and are amplified on this same line, and their purification is carried out from the infected cells. The cells are recovered by centrifugation (1500 rpm, 10 minutes) and lysed by 3 freeze/thaw cycles. The cell lysate is clarified by two centrifugations (2000 rpm, 10 minutes; 8000 rpm, 15 minutes), then purified by two successive ultracentrifugations. The first is carried out on a Caesium Chloride gradient (densities 1.4 and 1.25) at 30,000 rpm for 1 hour. The second is carried out on a Caesium Chloride cushion (density 1.34) at 35,000 rpm for 18 hours. The phases containing the virions are removed and diluted by half in a 60% saccharose buffer. The viral suspensions are then dialysed against formulation buffer (for 10 litres: 3423 g of saccharose; 12.11 g of Tris; 2.033 g of $MgCl_2$; 87.7 g of NaCl), then aliquoted. Their titration is carried out by indirect immunofluorescence on 293 cells infected by different viral dilutions and marked by an antibody specific to the adenoviral DNA-Binding Protein (α72K B6-8) (Reich, Sarnow, et al. 1983).

2. Preparation of the Adenovirus AdNS3NS4

This adenovirus allows the expression of the gene coding for the polyprotein NS3/NS4 (SEQ ID No. 1 and 2) under the control of the CMV promoter.

2.1 PCR Amplification of the Nucleotide Sequence Coding for the Polyprotein NS3/NS4

In order to do this, the following oligonucleotides were used:

```
oIV166:
                                              (SEQ ID No. 9)
5'-GGG GGG GCT ATG GCG CCT ATC ACG GCC TA-3' oIV171:
                                              (SEQ ID No. 10)
5'-GGG GGG ACG CGT TTA GCA TGG CGT GGA GCA GT-3'
``` as well as the following reagents:
Taq DNA Polymerase, PCR buffer, MgCl, 1.5 mM and dNTP 10 mM (Invitrogen).

The PCR conditions were the following:
5 minutes at 94° C., then
30 cycles of the series: 45 seconds at 94° C., 45 seconds at 62° C. and 1 minute at 72° C., then
10 minutes at 72° C.

2.2 Insertion of the PCR Fragment NS3/NS4 into the Transfer Plasmid pTG13387

The following stages were carried out:
Enzymatic digestion of the plasmid pTG13387 (FIG. 1A, Transgene) by NheI/MluI (NheI, Invitrogen in React 4 Buffer and MluI, Invitrogen in React 3 Buffer)
Enzymatic digestion of the fragment NS3/NS4 by NheI/MluI
Ligation (T4 DNA Ligase (Invitrogen) in Reaction Buffer (Invitrogen)),
Bacterial transformation (strain 5K, (Transgene)
Selection of bacterial clones on LB medium (Difco)+ampicillin (100 μg/ml, Duchefa)
Plasmid maxi-preparation (Qiagen, according to manufacturer's protocol) of a positive clone after restriction analysis
Restriction analysis: digestion by SmaI (Invitrogen in React 4 Buffer) and obtaining of fragments of: 5450, 2164, 909, 214 and 180 pb
Obtaining of the plasmid pIV315 deleted from its E1 region and containing the sequence NS3/NS4 under the control of the CMV promoter (FIG. 1B).

2.3 Homologous Recombination with the Complete Adenoviral Genome Deleted from its E3 Region Contained in the Plasmid pTG6624

The following stages were carried out:
Enzymatic digestion of the plasmid pIV315 obtained above by PacI/PvuI (PacI in NEB1 buffer, Biolabs and PvuI in React 7 Buffer, Invitrogen); isolation on agarose gel of the fragment containing the cassette pCMV-NS3-NS4
Enzymatic digestion of the plasmid pTG6624 (FIG. 1C) by ClaI (in React 1 Buffer, Invitrogen)
Bacterial transformation (strain BJ, (Transgene) in order to carry out the homologous recombination between the two plasmid fragments Selection of bacterial clones on LB medium+ampicillin (100 μg/ml)
Plasmid maxi-preparation (Qiagen) of a positive clone after restriction analysis
Restriction analysis: digestion by SmaI and obtaining of fragments of: 2263, 621, 3814, 214, 2164, 909, 180, 2463, 6480, 1398, 4456, 1455, 3540, 3386, 230 and 3685 pb
Obtaining of the complete adenoviral genome Adenovirus AdNS3NS4, deleted from its E3 and E1 regions, the latter having been replaced by the expression cassette pCMV-NS3-NS4 (pIV317, FIG. 1D).

3. Preparation of the Adenovirus AdNS3NS4NS5b

This adenovirus allows the expression of the gene coding for the polyprotein NS3/NS4 under the control of the CMV promoter and the expression of the gene coding for the polypeptide NS5b under the control of the SV40 promoter.

3.1 Construction of the Transfer Plasmid Allowing the Cloning in the E3 Region of the Adenovirus of a Coding Sequence Under the Control of the CMV Promoter The following stages were implemented:
Enzymatic digestion of the plasmid pTG4664 (FIG. 1E, Transgene) by BglII (in React 3 Buffer, Invitrogen)
Enzymatic digestion of the plasmid pTG3074 (FIG. 1F, Transgene) by BamHI/BglII (in React 3 Buffer, Invitrogen)
Ligation (T4 DNA ligase), bacterial transformation (strain 5K)
Selection of bacterial clones on LB medium+ampicillin (100 μg/ml)
Plasmid maxi-preparation (Qiagen) of a positive clone after restriction analysis
Restriction analysis: digestion by SmaI and obtaining of fragments of: 4940, 1305 and 230 pb
Obtaining of the plasmid pIV267 (FIG. 1G)
Digestion of the plasmid pIV267 thus obtained by ClaI/MunI (in React 1 Buffer, Invitrogen)
Treatment by DNA Polymerase I, Large (Klenow) Fragment (in React 2 Buffer, Invitrogen)
Ligation (T4 DNA Ligase)
Bacterial transformation (strain 5K)
Selection of bacterial clones on LB medium+ampicillin (100 μg/ml)
Plasmid maxi-preparation (Qiagen)
Restriction analysis: digestion by SmaI and obtaining of fragments of: 4692, 1305 and 230 pb
Obtaining of the plasmid pIV270, transfer plasmid allowing the cloning in the E3 region of the adenovirus of a coding sequence under the control of the CMV promoter (FIG. 1H).

3.2 Replacement of the CMV Promoter by the SV40 Promoter in pIV270

The following stages were carried out:
PCR amplification of the nucleotide fragment corresponding to the SV40 promoter, from the commercial plasmid pcDNAHygro (Clonetech) using the following oligonucleotides:

```
oIV232:
                                              (SEQ ID No. 11)
5'-GGG GGG AGA TCT CCA GCA GGC AGA AGT ATG-3' oIV233:
                                              (SEQ ID No. 12)
5'-GGG GGG GTC GAC CGA AAA TGG ATA TAC AAG CTC-3'
``` and according to the procedure described in point 2.1 above, except that a temperature of 58° C. instead of 62° C. was used
Enzymatic digestion of pIV270 by BglII/SalI (in React 10 Buffer, Invitrogen)
Enzymatic digestion of the PCR fragment by BglII/SalI Ligation (T4 DNA ligase), bacterial transformation (strain 5K)

Selection of the bacterial clones on LB medium+ampicillin (100 μg/ml)

Plasmid maxi-preparation (Qiagen) of a positive clone after restriction analysis Restriction analysis: digestion by SmaI and obtaining of fragments of: 4692, 719, 80 and 230 pb Obtaining of the plasmid pIV330, transfer plasmid allowing the cloning in the E3 region of the adenovirus of a coding sequence under the control of the SV40 promoter (FIG. 11).

3.3 Insertion of the PCR Fragment NS5b into the Transfer Plasmid pIV330

The following stages were carried out:

PCR amplification of the nucleotide sequence coding for the protein NS5b (SEQ ID No. 3 and 4) using the following nucleotides:

oIV212:
(SEQ ID No. 13)
5'-GGG GGG TCT AGA ATG TCA ATG TCC TAC ACA TGG AC-3' oIV218:
(SEQ ID No. 14)
5'-GGG GGG TCT AGA TTA CCG GTT GGG GAG CAG GT-3' and according to the procedure described in point 2.1 above, except that a temperature of 60° C. instead of 62° C. was used Enzymatic digestion of the plasmid pIV330 obtained above by XbaI (in React 2 Buffer, Invitrogen)

Enzymatic digestion of the PCR fragment by XbaI

Ligation (T4 DNA Ligase), bacterial transformation (strain 5K)

Selection of the bacterial clones on medium LB+ampicillin (100 μg/ml)

Plasmid maxi-preparation (Qiagen) of a positive clone after restriction analysis Restriction analysis: digestion by SmaI and obtaining of fragments of: 4692, 1505, 760, 719 and 230 pb Obtaining of the plasmid pIV336, transfer plasmid in the E3 deletion containing the sequence NS5b under the control of the SV40 promoter (FIG. 1J)

3.4 Homologous Recombination with the Recombinant Adenoviral Genome pIV317 in Order to Obtain the Adenovirus of the Title The following stages were implemented:

Digestion of the plasmid pIV317 obtained in point 2.3 above by SrfI (in Universal Buffer, Stratagene)

Digestion of the plasmid pIV336 obtained in point 3.3 by NheI/SacII (in Buffer T, Amersham Pharmacia Biotech) and isolation on agarose gel of the fragment containing the cassette pSV40-NS5b Bacterial transformation (strain BJ) for carrying out the homologous recombination between the two plasmid fragments Selection of the bacterial clones on medium LB+ampicillin (100 μg/ml)

Plasmid maxi-preparation (Qiagen) of a positive clone after restriction analysis Restriction analysis: digestion by SmaI and obtaining of fragments of: 6480, 4456, 3814, 3540, 3386, 2739, 2463, 2263, 2164, 1455, 1398, 1105, 909, 760, 719, 621, 230, 214 and 180 pb Obtaining of the desired complete adenoviral genome, deleted from the E1 region, the latter having been replaced by the expression cassette pCMV-NS3-NS4, and deleted from the E3 region, the latter having been replaced by the expression cassette pSV40-NS5B (plasmid pIV342, FIG. 1K).

4 Confirmation of the Expression of the Antigens Inserted into the Different Adenoviruses The expression of the HCV antigens encoded by the adenoviruses AdNS3NS4, AdNS5b and AdNS3NS4NS5b was verified by Western blot after infection of Huh7 cells.

As expected, all the antigens were expressed.

EXAMPLE 2

Preparation of a Poxvirus Allowing the Expression of the Proteins NS3/NS4 and NS5b According to the Invention 1. MVA Poxvirus The strain Modified Virus Ankara MVATG N33 was supplied by TRANSGENE S. A. (Strasbourg, France).

2. Preparation of the Transfer Plasmid Allowing the Expression of the Gene NS3/NS4 Under the Control of the ph5r Promoter 2.1 Construction of the pIV250 Vector Containing the Recombination Arms BRG2 and BRD2 of the MVA, as well as the selection gene GPT Under the Control of the Promoter ph5r (MVA), Followed by a Second Promoter ph5r in Order to Allow the Expression of the Gene of Interest At this point, the insertion of the fragment ph5r-GPT-BRG3-ph5r (originating from the plasmid pTG9997, Transgene) into the plasmid pTG6018 (Transgene) containing the recombination arms BRG2 and BRD2 is desired.

In order to do this, the following stages were carried out:

Enzymatic digestion by BamHI/SacI (in React 2 Buffer, Invitrogen) of the vector pTG6018 (FIG. 2A)

Enzymatic digestion by BamHI, then partial digestion by SacI of the plasmid pTG9997 (FIG. 2B)

Purification according to the QIAGEN protocol of the restriction fragment of 1047 pb that contains the sequence coding for ph5r-GPT-BRG3-ph5r Ligation (T4 DNA Ligase), bacterial transformation (strain TG1, Statagene)

Selection of the bacterial clones on ampicillin (100 μg/ml)

Plasmid maxi-preparation (Qiagen) of a positive clone after restriction analysis (EcoRV+HindIII (in React 2 Buffer, Invitrogen): fragments of 246, 439, 476, 826 and 2789 pb; SacI: fragments of 915 and 3861 pb)

Obtaining of the plasmid aimed at (pIV250, FIG. 2C).

2.2 PCR Amplification of the Nucleotide Sequence Coding for the Polyprotein NS3/NS4

The following oligonucleotides were used:

oIV225:
(SEQ ID No. 15)
5'-GGG GGG CTG CAG ATG GCG CCT ATC ACG GCC TA-3' oIV226:
(SEQ ID No. 16)
5'-GGG GGG TCT AGA TTA GCA TGG CGT GGA GCA GT-3' and according to the procedure described in Example 1, point 2.1 above, except that a temperature of 52° C. instead of 62° C. was used.

2.3 Insertion of the Fragment of PCR NS3-NS4 in the Plasmid pIV250

In order to do this, the following stages were carried out:

Enzymatic digestion of the plasmid pIV250 obtained in point 2.1 above by PstI (in React 2 Buffer, Invitrogen)/XbaI Enzymatic digestion of the PCR fragment NS3/NS4 by PstI/XbaI Ligation (T4 DNA Ligase), bacterial transformation (strain TG1)

Selection of the bacterial clones on ampicillin (100 µg/ml)

Plasmid maxi-preparation (Qiagen) of a positive clone after restriction analysis: (HindIII (in React 2 Buffer, Invitrogen): fragments of 4763 and 2789 pb; SphI (in React 6 Buffer, Invitrogen): 1534 and 5991 pb; NcoI (in React 3 Buffer, Invitrogen): 2764 and 4761 pb)

Obtaining of the transfer plasmid containing the sequence coding for the polyprotein NS3/NS4 under the control of the promoter ph5r (pIV327, FIG. 2D).

3. Preparation of the Plasmid pIV328 Allowing the Expression of the Protein NS5b Under the Control of the p7.5 Promoter 3.1 PCR Amplification of the Nucleotide Sequence Coding for the Protein NS5b The following nucleotides were used:

oIV227:
(SEQ ID No. 17)
5'-GGG GGG GTC GAC ATG TCA ATG TCC TAC ACA TGG AC-3' oIV228:
(SEQ ID No. 18)
5'-GGG GGG GCA TGC TTA CCG GTT GGG GAG CAG GT-3' and according to the procedure described in Example 1, point 2.1 above, except that a temperature of 52° C. instead of 62° C. was used.

3.2 Obtaining of the Plasmid

The following stages were carried out:

Enzymatic digestion of the PCR fragment coding for NS5b by SalI/SphI

Enzymatic digestion of pTG186 (FIG. 2E, Transgene) by SalI/SphI

Dephosphorylation of the vector pTG186 (ROCHE alkaline phosphatase)

Ligation (T4 DNA Ligase), bacterial transformation (strain TG1)

Selection of the bacterial clones on ampicillin (100 µg/ml)

Plasmid maxi-preparation (Qiagen) of a positive clone after restriction analysis: (HindIII: fragments of 1984, 2627 and 4437 pb; BglII: fragments of 321, 557, 1361, 1451, 2237 and 3121 pb; KpnI (in React 4 Buffer, Invitrogen): fragments of: 2787 and 6261 pb)

Obtaining of the transfer plasmid containing the sequence coding for the polypeptide NS5b under the control of the p7.5 promoter (pIV328, FIG. 2F).

4. Preparation of the Transfer Plasmids pIV329 and pIV344 Allowing the Expression of the Gene Coding for the Polyprotein NS3/NS4 Under the Control of the ph5r Promoter and of the Gene Coding for the Polyprotein NS3/NS4 under the Control of the p7.5 Promoter In order to do this the following stages were implemented:

PCR amplification of the nucleotide sequence coding for the protein NS5b from the plasmid pIV328 obtained in point 3.2 above using the following oligonucleotides:

oIV229:
(SEQ ID No. 19)
5'-GGG GGG TCT AGA CCG GTA GTT CGC ATA TAC ATA-3' oIV218:
(SEQ ID No. 14)
5'-GGG GGG TCT AGA TTA CCG GTT GGG GAG CAG GT-3' and according to the procedure described in Example 1, point 2.1 above, except that a temperature of 52° C. instead of 62° C. was used.

Enzymatic digestion of the fragment of PCR by XbaI

Enzymatic digestion of the plasmid pIV327 obtained in point 2.3 above by XbaI

Ligation (T4 DNA Ligase), bacterial transformation (strain TG1)

Selection of the bacterial clones on ampicillin (100 µg/ml)

Plasmid maxi-preparation (Qiagen) of 2 positive clones after restriction analysis: (PstI: pIV329: fragments of 3033 and 6466 pb, pIV344: 4641 and 4858 pb; ApaI (in React 4 Buffer, Invitrogen): pIV329: 454, 960 and 8085 pb, pIV344: 454, 1418 and 7627 pb; NcoI: pIV329: 4269, 469 and 4761 pb, pIV344: 3053, 1685 and 4761 pb; SmaI: pIV329: 214, 2164, 1444 and 5677 pb, pIV344: 214, 2164, 928 and 6193 pb)

Obtaining either of the transfer plasmid allowing the expression of the polyprotein NS3/NS4 under the control of the ph5r promoter and of the protein NS5b under the control of the p7.5 promoter, the 2 expression cassettes being oriented in the same direction (pIV329, FIG. 2G), or of the transfer plasmid allowing the expression of the polyprotein NS3/NS4 under the control of the ph5r promoter and of the protein NS5b under the control of the p7.5 promoter, the 2 expression cassettes being oriented in opposite directions (pIV344, FIG. 2H).

5. Confirmation of the Expression of the Antigens Inserted into the Different Poxviruses It was verified by Western blot, after infection of Huh7 cells with the poxviruses concerned, that the poxviruses pIV329 and pIV344, containing the sequences coding for the polyprotein NS3/NS4 and the polypeptide NS5b, expressed said HCV antigens.

EXAMPLE 3

Demonstration of the Immunogenicity of the Combination of NS3/NS4 and NS5b

1. Immunization of Mice

HLA-A2.1 transgenic mice were immunized, once, by intramuscular injection of at least one adenovirus chosen from the following adenoviruses:

AdNS3NS4 prepared in Example 1 above (point 2.3),

AdNS5 prepared in Example 1 above (point 3.3),

AdNS5a prepare according to the procedure of Example 1, point 2, except that the following nucleotide primers were used in order to amplify the nucleotide sequence coding for the polypeptide NS5a (SEQ ID No. 5 and 6):

oIV172:
(SEQ ID No. 20)
5'-GGG GGG GGT ACC ATG TCC GGC TCG TGG CTA AGG-3', oIV173:
(SEQ ID No. 21)
5'-GGG GGG TCT AGA TTA GCA GCA GAC GAT GTC GTC-3', in the PCR the temperature of 62° C. was replaced by 56° C., the enzymatic digestion of pTG 13387 and of the fragment NS5a were implemented by KpnI/XbaI, restriction analysis by digestion by SmaI of pTG13387 producing fragments of 180 and 7251 pb and of pTG6624 producing fragments of 2263, 621, 5615, 180, 2463, 6480, 1398, 4456, 1455, 3540, 3386, 230 and 3685 pb.

AdCE1 E2 according to the procedure of Example 1, point 2, except that the following nucleotide primers were used in order to amplify the nucleotide sequence coding for the core-E1-E2 polyprotein (also called CE1CE2) (SEQ ID No. 7 and 8):

oIV62:
(SEQ ID No. 22)
5'-GGG GGG GCT AGC ATG AGC ACA AAT CCT AAA CCT-3', oIV68:
(SEQ ID No. 23)
5'-GGG GGG TCT AGA TCA GGC CTC AGC CTG GGC TAT-3', in the PCR the temperature of 62° C. was replaced by 56° C., the enzymatic digestion of pTG13387 and of the fragment CE1CE2 were implemented by NheI/XbaI, restriction analysis by digestion by SmaI of pTG13387 producing fragments of 163, 435, 2270, 180 and 5254 pb and of pTG6624 producing fragments of 2263, 621, 3618, 163, 435, 2270, 180, 2463, 6480, 1398, 4456, 1455, 3540, 3386, 230 and 3685 pb, AdNS3NS4NS5b prepared in Example 1 above (point 3) and
AdβGal (Transgene),
according to the following protocol:
10$^9$ pfu of AdNS3NS4 or
10$^9$ pfu of AdNS5b or
10$^9$ pfu of AdCEIE2 or
10$^9$ pfu of AdNS3NS4 and 10$^9$ pfu of AdNS5b or
10$^9$ pfu of AdNS3NS4, 10$^9$ pfu of AdNS5b and 10$^9$ pfu of AdNS5a
10$^9$ pfu of AdNS3NS4, 109 pfu of AdNS5b and 10$^9$ pfu of AdCEIE2
10$^9$ pfu of AdNS3NS4 NS5b or
10$^9$ pfu of Adβ-Gal as control.

Before immunization, the expression of the HCV and β-Gal antigens by the different adenoviruses used for the immunization were verified by Western blot.

2. CTL and ELISPOT Tests

Fifteen days after injection, the cell response was analyzed by isolating the spleen cells (splenocytes) of the mice and a CTL test and an ELISPOT test were carried out as follows:

For the CTL test, these splenocytes were cultured on 24-well plates in the presence of:

5 μM of the epitope GLL (GLLGCIITSL, SEQ ID No. 24) in the case of the splenocytes originating from mice having received AdNS3NS4, 5 μM of the epitope ALY (ALYDV-VSTL, SEQ ID No. 25) or 5 μM of the epitope KLQ (KLQDCTMLV, SEQ ID No. 26) in the case of the splenocytes originating from mice having received AdNS5b or 5 μM of the epitope DLM (DLMGYIPLV, SEQ ID No. 27) in the case of the splenocytes originating from mice having received AdCE1E2, said epitopes being in synthetic peptide form (Eurogentex) and, 10 U of murine recombinant interleukin 2 (Brinster et al., Hepatology 2001) per ml in alpha minimum essential medium (αMEM) for 5 days. On the 5th day, the restimulation stage was carried out, which consists of adding naive mice splenocytes to the splenocytes in culture in the presence of said epitopes over 2 days. On the 7th day, the CTL test was carried out, which consists of bringing into contact the spienocytes from the immunized mice after 7 days of culture (effector cells) and EL4 S3-Rob HDD cells loaded with 10 μM of said epitopes and labelled with Cr$^{51}$ (target cells). The specific cytotoxic activity of the effector cells was determined by measuring, after 4 hours of incubation with the target cells, Cr$^{51}$ released following lysis of the target cells using a γ-Cobra II counting apparatus (Packard, Rungis, France) The maximum spontaneous release from wells containing either medium alone, or lysis buffer (HCl IN) was determined. The specific percentage of cytotoxicity was calculated by the formula:

(release in the test−spontaneous release)/(maximum release−spontaneous release)×100.

The epitope-specific lysis was determined by the difference between the percentage of specific lysis obtained in the presence or in the absence of said epitopes.

The ELISPOT test was carried out by culturing the splenocytes for 48 hours in Multiscreen 96-well plates (Millipore) previously coated with anti-interferon gamma antibodies (IFNγ) (10 μg/ml final). The splenocytes were cultured in the presence of 10 μM of the appropriate epitopes, as indicated above, and of 10 U of murine recombinant interleukin 2 per ml in αMEM. For the positive control, the splenocytes were cultured in the presence of concanavalin A (5 μg/ml). For the negative control, the splenocytes were cultured either in the presence of a non-specific peptide belonging to the capsid protein of HCV, of sequence DLMGYIPLV (also called irrelevant peptide), or in medium alone without epitope. The wells were washed three times, with 0.05% PBS-Tween then PBS respectively, an operation followed by incubation for 2 hours with anti-IFNγ antibodies from biotinylated mice. After washing, the wells were incubated for 1 hour with a streptavidine-horseradish peroxidase conjugate and the enzymatic activity was developed by degradation of the AEC (aminoethylcarbazole) substrate. The spots obtained were counted using a Zeiss ELISpot reader (Zeiss microscope in conjunction with the KS-ELISpot software).

The results are indicated in FIGS. 3 to 5 in which M corresponds to mouse and Neg. mouse corresponds to the control mouse.

These results demonstrate that

AdNS3NS4 clearly induces a cell-mediated response specific of the expressed antigens, as illustrated in FIGS. 3A and 3B by the detection of T lymphocytes specific to the epitope GLL contained in NS3.

AdNS5b clearly induces a cell-mediated response specific of the expressed antigens, as illustrated in FIG. 4 by the detection of T lymphocytes specific to the epitope ALY and KLQ contained in NS5b.

AdCEIE2 clearly induces a cell-mediated response specific of the expressed antigens, as illustrated in FIG. 5 by the detection of T lymphocytes specific to the epitope DLM contained in the Core protein.

3. In Vivo Trial Test Using a Recombinant Vaccinia Virus

In order to evaluate whether the specific immune responses induced by the different adenoviruses were capable of inducing protection against a infectious disease trial ("in vivo protection"), we subjected the vaccinated mice to such a trial.

The mice not being directly infectable by HCV, in order to link the induction of a specific immune response and resistance to an infection, we used a recombinant vaccinia virus (strain WR) coding for the non-structural proteins of HCV (NS2 to NS5b) in order to carry out this trial. This recombinant vaccinia virus, after intra-peritoneal injection of 10$^7$ pfu in the mouse, will be replicated in the animal. The replication of this virus induces an immune response both specific to the vaccinia antigens and specific to the HCV antigens, as it also expresses the NS proteins of HCV. This specific response to the HCV antigens will be all the more effective and vigorous as the mice will have already received a vaccine expressing the HCV antigens. In other words, the more the effective vaccination (in the present case carried out with the recombinant adenoviruses) has been (i.e. the immune system of the mice have been effectively "primed" by the vaccine), the stronger will be the anti-HCV response generated after trial by the recombinant vaccinia virus and, consequently, the more the mice are "protected" against this trial. In practice, the lower the residual vaccinia virus count in the mice, the more effective the protection or the neutralization due to the vaccination has been.

The neutralization of the vaccinia virus reflects both the cell response induced by the HCV proteins and by the vaccinia proteins. The neutralization is evaluated by titration of the residual vaccinia virus from the ovaries of the animals as follows: the ovaries are removed 4 days post-trial, sonicated, freeze-thawed 3 times then after centrifugation, successive dilutions of supernatant are titrated according to the lysis plaque technique (Murata et al., PNAS, vol. 100, p. 6753-6758) on Hutk-cells. The viral titres are determined in pfu/ml/mg of ovary.

4. Demonstration of Superior Protection of a Vaccination Combining The Polyprotein NS3/NS4 and the Polypeptide NS5b.

The recombinant virus titre of the vaccine was determined for 4 groups of 8 mice immunized by the following combinations of adenoviruses: AdNS3NS4+AdNS5b (1st group), AdNS3NS4+AdNS5b+AdNS5a (2nd group), AdNS3NS4+AdNS5b+AdCEIE2 (3rd group) and AdβGal (4th group).

The results, given in FIG. 6, are treated statistically on the basis of the Wilcoxon Mann-Whitney non-parametric test (Méthodes Statistiques á l'usage des médecins et des biologistes, Collection Statistique en Biologie et en Médecine, Flammarion Medecine Sciences, (D. Schwarz), 1977), which is based on a comparison of the averages, and allows the comparison of the values of two independent samples x and y.

This test is implemented as follows: all of the values of the two groups x and y to be compared are classified in increasing fashion. A rank is then allocated to each value, and the sum of the ranks is calculated. Wx and Wy are then obtained. A reference value called $(Wx)_t$ (theoretical value in the null hypothesis where Wx is not different from Wy) is then calculated and linked by the ratio: n (N+1)/2, with n=number of mice tested in group$_x$ and N=number of mice tested in groups x and y.

If $W_x$ is less than $(Wx)_t$ (low residual level of vaccinia virus in the mice), then it can be concluded that the neutralization resulting from the vaccination is significantly effective.

If we take the example of the group AdNS3NS4S5b denoted x compared with the group AdβGal denoted y, we obtain the following values:

Wx=1+2+4+6+8+11+13+14=59 (8 mice tested)
Wy=3+5+7+9+10+12+15+16=77 (8 mice tested)

Under the null hypothesis, Wx is not different from Wy, the expected value is: $(Wx)_t=(½)*8*17=68$ Wx<$(Wx)_t$, which signifies that the values obtained in the group AdNS3NS4NS5b are smaller than those obtained in the group AdβGal and that the neutralization resulting from the vaccination is significantly effective.

The statistical values for the other groups of mice are indicated in Table 1 below:

TABLE 1

| Group/AdβGal | Wx | $(Wx)_t$ |
|---|---|---|
| AdNS3NS4 + NS5b | 52 | 68 |
| AdNS3NS4 + NS5b + NS5a | 68 | 68 |
| AdNS3NS4 + NS5b + CE1E2 | 74 | 68 |

The values in Table 1 above show that only a vaccination of the mice by a combination of the Adenoviruses NS3NS4 and adenovirus NS5b is capable of inducing a significant neutralization of the replication of the vaccinia virus used in the trial with respect to the group of control mice vaccinated by AdβGal. The vaccinations carried out using the combinations comprising (AdNS3NS4+AdNS5b+AdNS5a) or (AdNS3NS4+AdNS5b+AdCE1 E2), do not result in a significant difference compared with the group of control mice immunized by AdβGal.

These results therefore make it possible to demonstrate, unexpectedly, the superior protection of a vaccination combining the polyprotein NS3NS4 and the polypeptide NS5b.

5. Confirmation of the Protection of a Vaccination Combining the Polyprotein NS3NS4 and the Polypeptide NS5b Expressed Jointly by the Same Vector The recombinant vaccinia virus titre was determined for 3 groups of 8 mice immunized by the following combinations of adenoviruses: AdNS3NS4AdNS5b (1st group), AdNS3NS4+AdNS5b (2nd group), and AdβGal (3rd group).

The results, given in FIG. 7, are treated statistically on the basis of the Wilcoxon Mann-Whitney non-parametric test as described in the previous experiment.

The statistical values for groups 1 and 2 compared to the control group AdβGal are indicated in Table 2 below:

TABLE 2

| Group/AdβGal | Wx | $(Wx)_t$ |
|---|---|---|
| AdNS3NS4NS5b | 49 | 68 |
| AdNS3NS4 + NS5b | 53 | 68 |

The values in Table 2 above show that the vaccination of the mice by an adenovirus coding both for the three antigens NS3, NS4 et NS5b, like the combination of the Adenovirus NS3NS4 and Adenovirus NS5b, is capable of inducing a significant neutralization of the replication of the vaccinia virus used in the trial with respect to the group of control mice vaccinated by the AdenoβGal. This result confirms the protection of a vaccination combining the polyprotein NS3/NS4 and the polypeptide NS5b expressed jointly by the same vector.

The invention claimed is:

1. An expression vector into which is inserted only two nucleotide sequences originating from one or more hepatitis C virus(es), which consist of (a) a nucleotide sequence encoding a polyprotein NS3/NS4 of the hepatitis C virus placed under regulatory elements necessary to its expression and (b) a nucleotide sequence encoding a polypeptide NS5b of the hepatitis C virus placed under regulatory elements necessary to its expression wherein the polyprotein NS3/NS4 and polypeptide of NS5b are not expressed as a fusion protein.

2. The expression vector according to claim 1, characterized in that the nucleotide sequences encode the polyprotein and the polypeptide from hepatitis C viruses of different genotypes.

3. The expression vector according to claim 1, characterized in that the nucleotide sequences encode the polyprotein and the polypeptide originating from a hepatitis C virus of the same genotype, preferably the genotype 1b.

4. The expression vector according to claim 1, characterized in that this vector is an adenovirus.

5. The expression vector according to claim 4, characterized in that the genome of the adenovirus is modified so as to replace the EI region by the expression cassette CMV-NS3-NS4 and to replace the E3 region by the expression cassette SV40-NS5b.

6. The expression vector according to claim 1, characterized in that this vector is a poxvirus, in particular a modified vaccinia virus Ankara (MVA).

7. The expression vector according to claim 6, characterized in that the genome of the poxvirus is modified so as to insert the expression cassette ph5r-NS3-NS4 and expression cassette p7.5-NS5b.

8. An isolated microorganism or host cell transformed by an expression vector as defined in claim 1.

9. An isolated microorganism or host cell transformed by an expression vector as defined in claim 6.

10. A pharmaceutical composition comprising as active ingredient the expression vector as defined in claim 1.

11. The pharmaceutical composition according to claim 10, characterized in that it also comprises a pharmaceutically appropriate vehicle.

12. A pharmaceutical kit comprising the expression vector of claim 1.

13. A pharmaceutical kit comprising:
at least two expression vectors according to claim 1,
wherein at least one of said at least two expression vectors is an adenovirus expression vector, and
wherein at least one of said at least two expression vectors is a poxvirus expression vector.

14. A pharmaceutical composition comprising the expression vector as defined in claim 6.

15. The pharmaceutical composition according to claim 14, wherein said composition comprises a pharmaceutically appropriate vehicle.

16. A pharmaceutical kit comprising at least one expression vector as defined in claim 6.

17. An isolated viral particle comprising an expression vector as defined in claim 1.

18. An isolated viral particle comprising an expression vector as defined in claim 6.

19. A method for treating an infection caused by the hepatitis C virus in an animal, preferably human, comprising administering to said animal an expression vector as defined in claim 1.

20. A method for treating an infection caused by the hepatitis C virus in an animal comprising administering to said animal an expression vector as defined in claim 6.

21. The method as defined in claim 6, wherein said animal is a human.

* * * * *

SEQUENCE LISTING

<160> NUMBER OF SEQ ID NOS: 27

<210> SEQ ID NO 1
<211> LENGTH: 2844
<212> TYPE: DNA
<213> ORGANISM: Artificial sequence
<220> FEATURE:
<223> OTHER INFORMATION: sequence coding for NS3NS4
<220> FEATURE:
<221> NAME/KEY: CDS
<222> LOCATION: (1)..(2844)
<223> OTHER INFORMATION:

<400> SEQUENCE: 1

```
atg gcg cct atc acg gcc tat tcc caa caa acg cgg ggc ctg ctt ggc      48
Met Ala Pro Ile Thr Ala Tyr Ser Gln Gln Thr Arg Gly Leu Leu Gly
1               5                   10                  15 tgt atc atc act agc ctc aca ggt cgg gac aag aac cag gtc gat ggg      96
Cys Ile Ile Thr Ser Leu Thr Gly Arg Asp Lys Asn Gln Val Asp Gly
                20                  25                  30 gag gtt cag gtg ctc tcc acc gca acg caa tct ttc ctg gcg acc tgc     144
Glu Val Gln Val Leu Ser Thr Ala Thr Gln Ser Phe Leu Ala Thr Cys
            35                  40                  45 gtc aat ggc gtg tgt tgg acc gtc tac cat ggt gcc ggc tcg aag acc     192
Val Asn Gly Val Cys Trp Thr Val Tyr His Gly Ala Gly Ser Lys Thr
        50                  55                  60 ctg gcc ggc ccg aag ggt cca atc acc caa atg tac acc aat gta gac     240
Leu Ala Gly Pro Lys Gly Pro Ile Thr Gln Met Tyr Thr Asn Val Asp
65                  70                  75                  80 cag gac ctc gtc ggc tgg ccg gcg ccc ccc ggg gcg cgc tcc atg aca     288
Gln Asp Leu Val Gly Trp Pro Ala Pro Pro Gly Ala Arg Ser Met Thr
                85                  90                  95 ccg tgc acc tgc ggc agc tcg gac ctt tac ttg gtc acg agg cat gcc     336
Pro Cys Thr Cys Gly Ser Ser Asp Leu Tyr Leu Val Thr Arg His Ala
                100                 105                 110 gat gtc att ccg gtg cgc cgg cga ggc gac agc agg ggg agt cta ctc     384
Asp Val Ile Pro Val Arg Arg Arg Gly Asp Ser Arg Gly Ser Leu Leu
            115                 120                 125 tcc cct agg ccc gtc tcc tac ctg aag ggc tcc tcg ggt gga cca ctg     432
Ser Pro Arg Pro Val Ser Tyr Leu Lys Gly Ser Ser Gly Gly Pro Leu
        130                 135                 140 ctt tgc cct tcg ggg cac gtt gta ggc atc ttc cgg gct gct gtg tgc     480
Leu Cys Pro Ser Gly His Val Val Gly Ile Phe Arg Ala Ala Val Cys
145                 150                 155                 160 acc cgg ggg gtt gcg aag gcg gtg gac ttc ata ccc gtt gag tct atg     528
Thr Arg Gly Val Ala Lys Ala Val Asp Phe Ile Pro Val Glu Ser Met
                165                 170                 175 gaa act acc atg cgg tct ccg gtc ttc aca gac aac tca tcc cct ccg     576
Glu Thr Thr Met Arg Ser Pro Val Phe Thr Asp Asn Ser Ser Pro Pro
                180                 185                 190 gcc gta ccg caa aca ttc caa gtg gca cat tta cac gct ccc act ggc     624
Ala Val Pro Gln Thr Phe Gln Val Ala His Leu His Ala Pro Thr Gly
            195                 200                 205 agc ggc aag agc acc aaa gtg ccg gct gca tat gca gcc caa ggg tac     672
Ser Gly Lys Ser Thr Lys Val Pro Ala Ala Tyr Ala Ala Gln Gly Tyr
        210                 215                 220 aag gtg ctc gtc cta aac ccg tcc gtt gct gcc aca ttg ggc ttt gga     720
Lys Val Leu Val Leu Asn Pro Ser Val Ala Ala Thr Leu Gly Phe Gly
225                 230                 235                 240 gcg tat atg tcc aag gca cat ggc atc gag cct aac atc aga act ggg     768
Ala Tyr Met Ser Lys Ala His Gly Ile Glu Pro Asn Ile Arg Thr Gly
                245                 250                 255 gta agg acc atc acc acg ggc ggc ccc atc acg tac tcc acc tat ggc     816
Val Arg Thr Ile Thr Thr Gly Gly Pro Ile Thr Tyr Ser Thr Tyr Gly
                260                 265                 270 aag ttc ctt gcc gac ggt gga tgc tcc ggg ggc gcc tat gac atc ata     864
Lys Phe Leu Ala Asp Gly Gly Cys Ser Gly Gly Ala Tyr Asp Ile Ile
            275                 280                 285
```

| | | |
|---|---|---|
| ata tgt gac gaa tgc cac tca act gac tgg aca acc atc ttg ggc atc<br>Ile Cys Asp Glu Cys His Ser Thr Asp Trp Thr Thr Ile Leu Gly Ile<br>290                             295                               300 | 912 |
| ggc aca gtc ctg gat cag gca gag acg gct gga gcg cgg ctc gtc gtg<br>Gly Thr Val Leu Asp Gln Ala Glu Thr Ala Gly Ala Arg Leu Val Val<br>305                           310                         315                       320 | 960 |
| ctc gcc acc gcc acg cct ccg gga tcg atc acc gtg cca cac ccc aac<br>Leu Ala Thr Ala Thr Pro Pro Gly Ser Ile Thr Val Pro His Pro Asn<br>                           325                         330                       335 | 1008 |
| atc gag gaa gtg gcc ctg tcc aac act ggg gag att ccc ttc tat ggc<br>Ile Glu Glu Val Ala Leu Ser Asn Thr Gly Glu Ile Pro Phe Tyr Gly<br>                340                         345                       350 | 1056 |
| aaa gcc atc ccc att gag gcc atc aag ggg gga agg cat ctc atc ttc<br>Lys Ala Ile Pro Ile Glu Ala Ile Lys Gly Gly Arg His Leu Ile Phe<br>                    355                       360                       365 | 1104 |
| tgc cat tcc aag aag aag tgt gac gag ctc gcc gca aag ctg aca ggc<br>Cys His Ser Lys Lys Lys Cys Asp Glu Leu Ala Ala Lys Leu Thr Gly<br>370                             375                         380 | 1152 |
| ctc gga ctc aat gct gta gcg tat tac cgg ggt ctc gat gtg tcc gtc<br>Leu Gly Leu Asn Ala Val Ala Tyr Tyr Arg Gly Leu Asp Val Ser Val<br>385                           390                         395                       400 | 1200 |
| ata ccg act agc gga gac gtc gtt gtc gtg gca aca gac gct cta atg<br>Ile Pro Thr Ser Gly Asp Val Val Val Val Ala Thr Asp Ala Leu Met<br>                         405                       410                       415 | 1248 |
| acg ggc ttt acc ggc gac ttt gac tca gtg atc gac tgc aac aca tgt<br>Thr Gly Phe Thr Gly Asp Phe Asp Ser Val Ile Asp Cys Asn Thr Cys<br>                420                         425                       430 | 1296 |
| gtc acc cag aca gtc gat ttc agc ttg gat ccc acc ttc acc att gag<br>Val Thr Gln Thr Val Asp Phe Ser Leu Asp Pro Thr Phe Thr Ile Glu<br>                    435                       440                       445 | 1344 |
| acg aca acc gtg ccc caa gac gcg gtg tcg cgc tcg cag cgg cga ggt<br>Thr Thr Thr Val Pro Gln Asp Ala Val Ser Arg Ser Gln Arg Arg Gly<br>450                             455                         460 | 1392 |
| agg act ggc agg ggc agg agt ggc atc tac agg ttt gtg act cca gga<br>Arg Thr Gly Arg Gly Arg Ser Gly Ile Tyr Arg Phe Val Thr Pro Gly<br>465                           470                         475                       480 | 1440 |
| gaa cgg ccc tca ggc atg ttc gac tcc tcg gtc ctg tgt gag tgc tat<br>Glu Arg Pro Ser Gly Met Phe Asp Ser Ser Val Leu Cys Glu Cys Tyr<br>                    485                       490                       495 | 1488 |
| gac gca ggc tgc gct tgg tat gag ctc acg ccc gct gag act aca gtc<br>Asp Ala Gly Cys Ala Trp Tyr Glu Leu Thr Pro Ala Glu Thr Thr Val<br>                500                       505                       510 | 1536 |
| agg ttg cgg gct tac ctg aat aca cca ggg ttg ccc gtc tgc cag gac<br>Arg Leu Arg Ala Tyr Leu Asn Thr Pro Gly Leu Pro Val Cys Gln Asp<br>            515                       520                       525 | 1584 |
| cat ctg gag ttc tgg gaa agc gtc ttc aca ggc ctc acc cac ata gat<br>His Leu Glu Phe Trp Glu Ser Val Phe Thr Gly Leu Thr His Ile Asp<br>530                             535                         540 | 1632 |
| gcc cac ttc ctg tcc caa acc aag cag gca gga gac aac ttc ccc tac<br>Ala His Phe Leu Ser Gln Thr Lys Gln Ala Gly Asp Asn Phe Pro Tyr<br>545                           550                         555                       560 | 1680 |
| ctg gtg gca tac caa gcc acg gtg tgc gcc agg gct cag gct cca cct<br>Leu Val Ala Tyr Gln Ala Thr Val Cys Ala Arg Ala Gln Ala Pro Pro<br>                    565                       570                       575 | 1728 |
| cca tcg tgg gat caa atg tgg aag tgt ctc ata cgg ctt aaa cct acg<br>Pro Ser Trp Asp Gln Met Trp Lys Cys Leu Ile Arg Leu Lys Pro Thr<br>                    580                       585                       590 | 1776 |
| ctg cac ggg cca aca ccc ctg ctg tat agg cta gga gcc gtt caa aat<br>Leu His Gly Pro Thr Pro Leu Leu Tyr Arg Leu Gly Ala Val Gln Asn<br>                    595                       600                       605 | 1824 |

```
gag atc acc ctc aca cat ccc ata acc aaa ttc gtc atg gca tgc atg    1872
Glu Ile Thr Leu Thr His Pro Ile Thr Lys Phe Val Met Ala Cys Met
    610                 615                 620 tcg gcc gac ctg gag gtc gtc act agc acc tgg gtg ctg gta ggc gga    1920
Ser Ala Asp Leu Glu Val Val Thr Ser Thr Trp Val Leu Val Gly Gly
625                 630                 635                 640 gtc ctt gca gct ctg gcc gca tat tgc ctg aca acc ggt agt gtg gtc    1968
Val Leu Ala Ala Leu Ala Ala Tyr Cys Leu Thr Thr Gly Ser Val Val
                645                 650                 655 att gtg ggt agg atc att ttg tcc ggg agg ccg gct gtt gtt ccc gac    2016
Ile Val Gly Arg Ile Ile Leu Ser Gly Arg Pro Ala Val Val Pro Asp
            660                 665                 670 agg gaa gtc ctc tac cgg gag ttc gat gaa atg gaa gag tgc gcc tca    2064
Arg Glu Val Leu Tyr Arg Glu Phe Asp Glu Met Glu Glu Cys Ala Ser
        675                 680                 685 cac ctc cct tac atc gag caa gga atg cag ctc gcc gag cag ttc aag    2112
His Leu Pro Tyr Ile Glu Gln Gly Met Gln Leu Ala Glu Gln Phe Lys
    690                 695                 700 cag cag gca ctc ggg ttg ctg caa aca gcc acc aag caa gcg gag gcc    2160
Gln Gln Ala Leu Gly Leu Leu Gln Thr Ala Thr Lys Gln Ala Glu Ala
705                 710                 715                 720 gct gct ccc gtg gtg gag tcc agg tgg cgg gcc ctt gag gcc ttc tgg    2208
Ala Ala Pro Val Val Glu Ser Arg Trp Arg Ala Leu Glu Ala Phe Trp
                725                 730                 735 gca aag cac atg tgg aac ttc atc agc ggg ata cag tac tta gca ggc    2256
Ala Lys His Met Trp Asn Phe Ile Ser Gly Ile Gln Tyr Leu Ala Gly
            740                 745                 750 tta tcc act ctg cct ggg aac ccc gcg ata gca tca ctg atg gca ttc    2304
Leu Ser Thr Leu Pro Gly Asn Pro Ala Ile Ala Ser Leu Met Ala Phe
        755                 760                 765 aca gcc tct atc acc agt ccg ctc acc acc cag aat acc ctc cta ttc    2352
Thr Ala Ser Ile Thr Ser Pro Leu Thr Thr Gln Asn Thr Leu Leu Phe
    770                 775                 780 aac atc tta ggg gga tgg gtg gct gct caa ctc gct cct ccc agt gct    2400
Asn Ile Leu Gly Gly Trp Val Ala Ala Gln Leu Ala Pro Pro Ser Ala
785                 790                 795                 800 gct tcg gcc ttc gtg ggt gcc ggc att gcc ggt gcg gcc att ggc agc    2448
Ala Ser Ala Phe Val Gly Ala Gly Ile Ala Gly Ala Ala Ile Gly Ser
                805                 810                 815 ata ggc ctt ggg aag gtg ctt gtg gac att ctg gcg ggc tat gga gcg    2496
Ile Gly Leu Gly Lys Val Leu Val Asp Ile Leu Ala Gly Tyr Gly Ala
            820                 825                 830 ggg gtg gcc ggt gca ctc gtg gct ttt aag gtc atg agc ggc gag gcg    2544
Gly Val Ala Gly Ala Leu Val Ala Phe Lys Val Met Ser Gly Glu Ala
        835                 840                 845 ccc tcc gcc gag gac ctg gtt aac ttg ctc cct gcc atc ctc tcc ccc    2592
Pro Ser Ala Glu Asp Leu Val Asn Leu Leu Pro Ala Ile Leu Ser Pro
    850                 855                 860 ggc gcc ttg gtc gtc ggg atc gtg tgt gca gca atc ctg cgt cgg cac    2640
Gly Ala Leu Val Val Gly Ile Val Cys Ala Ala Ile Leu Arg Arg His
865                 870                 875                 880 gtg ggc ccg gga gag ggg gct gtg cag tgg atg aac cgg ctg ata gcg    2688
Val Gly Pro Gly Glu Gly Ala Val Gln Trp Met Asn Arg Leu Ile Ala
                885                 890                 895 ttc gct tcg cgg ggt aac cac gtt tcc ccc acg cac tac gtg cct gag    2736
Phe Ala Ser Arg Gly Asn His Val Ser Pro Thr His Tyr Val Pro Glu
            900                 905                 910 agc gac gcc gca gca cgt gta act cag atc ctc tcc agc ctc acc atc    2784
Ser Asp Ala Ala Ala Arg Val Thr Gln Ile Leu Ser Ser Leu Thr Ile
        915                 920                 925
```

-continued

```
act cag ctg ctg aag agg ctt cac cag tgg att aat gag gac tgc tcc    2832
Thr Gln Leu Leu Lys Arg Leu His Gln Trp Ile Asn Glu Asp Cys Ser
        930                 935                 940 acg cca tgc taa                                                    2844
Thr Pro Cys
945

<210> SEQ ID NO 2
<211> LENGTH: 947
<212> TYPE: PRT
<213> ORGANISM: Artificial sequence
<220> FEATURE:
<223> OTHER INFORMATION: sequence coding for NS3NS4

<400> SEQUENCE: 2

Met Ala Pro Ile Thr Ala Tyr Ser Gln Gln Thr Arg Gly Leu Leu Gly
1               5                   10                  15

Cys Ile Ile Thr Ser Leu Thr Gly Arg Asp Lys Asn Gln Val Asp Gly
            20                  25                  30

Glu Val Gln Val Leu Ser Thr Ala Thr Gln Ser Phe Leu Ala Thr Cys
        35                  40                  45

Val Asn Gly Val Cys Trp Thr Val Tyr His Gly Ala Gly Ser Lys Thr
    50                  55                  60

Leu Ala Gly Pro Lys Gly Pro Ile Thr Gln Met Tyr Thr Asn Val Asp
65                  70                  75                  80

Gln Asp Leu Val Gly Trp Pro Ala Pro Pro Gly Ala Arg Ser Met Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140

Leu Cys Pro Ser Gly His Val Val Gly Ile Phe Arg Ala Ala Val Cys
145                 150                 155                 160

Thr Arg Gly Val Ala Lys Ala Val Asp Phe Ile Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Thr Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Glu Pro Asn Ile Arg Thr Gly
                245                 250                 255

Val Arg Thr Ile Thr Thr Gly Gly Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Trp Thr Thr Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Ile Thr Val Pro His Pro Asn
```

```
                        325                 330                 335
Ile Glu Glu Val Ala Leu Ser Asn Thr Gly Glu Ile Pro Phe Tyr Gly
                340                 345                 350
Lys Ala Ile Pro Ile Glu Ala Ile Lys Gly Gly Arg His Leu Ile Phe
                355                 360                 365
Cys His Ser Lys Lys Cys Asp Glu Leu Ala Ala Lys Leu Thr Gly
            370                 375                 380
Leu Gly Leu Asn Ala Val Ala Tyr Tyr Arg Gly Leu Asp Val Ser Val
385                 390                 395                 400
Ile Pro Thr Ser Gly Asp Val Val Val Ala Thr Asp Ala Leu Met
                    405                 410                 415
Thr Gly Phe Thr Gly Asp Phe Asp Ser Val Ile Asp Cys Asn Thr Cys
                420                 425                 430
Val Thr Gln Thr Val Asp Phe Ser Leu Asp Pro Thr Phe Thr Ile Glu
            435                 440                 445
Thr Thr Thr Val Pro Gln Asp Ala Val Ser Arg Ser Gln Arg Gly
            450                 455                 460
Arg Thr Gly Arg Gly Arg Ser Gly Ile Tyr Arg Phe Val Thr Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Thr Val
                500                 505                 510
Arg Leu Arg Ala Tyr Leu Asn Thr Pro Gly Leu Pro Val Cys Gln Asp
                515                 520                 525
His Leu Glu Phe Trp Glu Ser Val Phe Thr Gly Leu Thr His Ile Asp
                530                 535                 540
Ala His Phe Leu Ser Gln Thr Lys Gln Ala Gly Asp Asn Phe Pro Tyr
545                 550                 555                 560
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
                580                 585                 590
Leu His Gly Pro Thr Pro Leu Leu Tyr Arg Leu Gly Ala Val Gln Asn
                595                 600                 605
Glu Ile Thr Leu Thr His Pro Ile Thr Lys Phe Val Met Ala Cys Met
                610                 615                 620
Ser Ala Asp Leu Glu Val Val Thr Ser Thr Trp Val Leu Val Gly Gly
625                 630                 635                 640
Val Leu Ala Ala Leu Ala Ala Tyr Cys Leu Thr Thr Gly Ser Val Val
                645                 650                 655
Ile Val Gly Arg Ile Ile Leu Ser Gly Arg Pro Ala Val Val Pro Asp
                660                 665                 670
Arg Glu Val Leu Tyr Arg Glu Phe Asp Glu Met Glu Glu Cys Ala Ser
                675                 680                 685
His Leu Pro Tyr Ile Glu Gln Gly Met Gln Leu Ala Glu Gln Phe Lys
                690                 695                 700
Gln Gln Ala Leu Gly Leu Leu Gln Thr Ala Thr Lys Gln Ala Glu Ala
705                 710                 715                 720
Ala Ala Pro Val Val Glu Ser Arg Trp Arg Ala Leu Glu Ala Phe Trp
                    725                 730                 735
Ala Lys His Met Trp Asn Phe Ile Ser Gly Ile Gln Tyr Leu Ala Gly
                740                 745                 750
```

-continued

```
Leu Ser Thr Leu Pro Gly Asn Pro Ala Ile Ala Ser Leu Met Ala Phe
            755                 760                 765

Thr Ala Ser Ile Thr Ser Pro Leu Thr Thr Gln Asn Thr Leu Leu Phe
        770                 775                 780

Asn Ile Leu Gly Gly Trp Val Ala Ala Gln Leu Ala Pro Pro Ser Ala
785                 790                 795                 800

Ala Ser Ala Phe Val Gly Ala Gly Ile Ala Gly Ala Ala Ile Gly Ser
                805                 810                 815

Ile Gly Leu Gly Lys Val Leu Val Asp Ile Leu Ala Gly Tyr Gly Ala
            820                 825                 830

Gly Val Ala Gly Ala Leu Val Ala Phe Lys Val Met Ser Gly Glu Ala
                835                 840                 845

Pro Ser Ala Glu Asp Leu Val Asn Leu Leu Pro Ala Ile Leu Ser Pro
    850                 855                 860

Gly Ala Leu Val Val Gly Ile Val Cys Ala Ala Ile Leu Arg Arg His
865                 870                 875                 880

Val Gly Pro Gly Glu Gly Ala Val Gln Trp Met Asn Arg Leu Ile Ala
                885                 890                 895

Phe Ala Ser Arg Gly Asn His Val Ser Pro Thr His Tyr Val Pro Glu
            900                 905                 910

Ser Asp Ala Ala Arg Val Thr Gln Ile Leu Ser Ser Leu Thr Ile
        915                 920                 925

Thr Gln Leu Leu Lys Arg Leu His Gln Trp Ile Asn Glu Asp Cys Ser
    930                 935                 940

Thr Pro Cys
945

<210> SEQ ID NO 3
<211> LENGTH: 1779
<212> TYPE: DNA
<213> ORGANISM: Artificial sequence
<220> FEATURE:
<223> OTHER INFORMATION: sequence coding for NS5b
<220> FEATURE:
<221> NAME/KEY: CDS
<222> LOCATION: (1)..(1779)
<223> OTHER INFORMATION:

<400> SEQUENCE: 3 atg tca atg tcc tac aca tgg aca ggt gcc ttg atc acg cca tgc gct     48
Met Ser Met Ser Tyr Thr Trp Thr Gly Ala Leu Ile Thr Pro Cys Ala
1               5                   10                  15 gcg gag gag agc aag ttg ccc atc aat ccg ttg agc aac tct ttg ctg     96
Ala Glu Glu Ser Lys Leu Pro Ile Asn Pro Leu Ser Asn Ser Leu Leu
            20                  25                  30 cgt cac cac agt atg gtc tac tcc aca aca tct cgc agc gca agt ctg    144
Arg His His Ser Met Val Tyr Ser Thr Thr Ser Arg Ser Ala Ser Leu
        35                  40                  45 cgg cag aag aag gtc acc ttt gac aga ctg caa gtc ctg gac gac cac    192
Arg Gln Lys Lys Val Thr Phe Asp Arg Leu Gln Val Leu Asp Asp His
    50                  55                  60 tac cgg gac gtg ctc aag gag atg aag gcg aag gcg tcc aca gtt aag    240
Tyr Arg Asp Val Leu Lys Glu Met Lys Ala Lys Ala Ser Thr Val Lys
65                  70                  75                  80 gct agg ctt cta tct ata gag gag gcc tgc aaa ctg acg ccc cca cat    288
Ala Arg Leu Leu Ser Ile Glu Glu Ala Cys Lys Leu Thr Pro Pro His
                85                  90                  95 tcg gcc aaa tcc aaa ttt ggc tac ggg gcg aag gac gtc cgg agc cta    336
Ser Ala Lys Ser Lys Phe Gly Tyr Gly Ala Lys Asp Val Arg Ser Leu
            100                 105                 110
```

| | | | | | | | | | | | | | | | | |
|---|---|---|---|---|---|---|---|---|---|---|---|---|---|---|---|---|
| tcc | agc | agg | gcc | gtc | aac | cac | atc | cgc | tcc | gtg | tgg | gag | gac | ttg | ctg | 384 |
| Ser | Ser | Arg | Ala | Val | Asn | His | Ile | Arg | Ser | Val | Trp | Glu | Asp | Leu | Leu | |
| | 115 | | | | 120 | | | | | 125 | | | | | | |
| gaa | gac | act | gaa | aca | cca | att | gat | acc | acc | atc | atg | gca | aaa | aat | gag | 432 |
| Glu | Asp | Thr | Glu | Thr | Pro | Ile | Asp | Thr | Thr | Ile | Met | Ala | Lys | Asn | Glu | |
| 130 | | | | | 135 | | | | | 140 | | | | | | |
| gtt | ttc | tgc | gtc | caa | cca | gag | aaa | gga | ggc | cgc | aag | cca | gct | cgc | ctt | 480 |
| Val | Phe | Cys | Val | Gln | Pro | Glu | Lys | Gly | Gly | Arg | Lys | Pro | Ala | Arg | Leu | |
| 145 | | | | | 150 | | | | | 155 | | | | | 160 | |
| atc | gta | ttc | cca | gac | ctg | ggg | gta | cgt | gta | tgc | gag | aag | atg | gcc | ctt | 528 |
| Ile | Val | Phe | Pro | Asp | Leu | Gly | Val | Arg | Val | Cys | Glu | Lys | Met | Ala | Leu | |
| | | | | 165 | | | | | 170 | | | | | 175 | | |
| tac | gac | gtg | gtc | tcc | acc | ctt | cct | cag | gcc | gtg | atg | ggc | ccc | tca | tac | 576 |
| Tyr | Asp | Val | Val | Ser | Thr | Leu | Pro | Gln | Ala | Val | Met | Gly | Pro | Ser | Tyr | |
| | | | 180 | | | | | 185 | | | | | 190 | | | |
| gga | ttc | cag | tac | tct | cct | ggg | cag | cgg | gtc | gag | ttc | ctg | gtg | aat | acc | 624 |
| Gly | Phe | Gln | Tyr | Ser | Pro | Gly | Gln | Arg | Val | Glu | Phe | Leu | Val | Asn | Thr | |
| | | 195 | | | | | 200 | | | | | 205 | | | | |
| tgg | aaa | tca | aag | aaa | tgc | cct | atg | ggc | ttc | tca | tat | gac | acc | cgc | tgc | 672 |
| Trp | Lys | Ser | Lys | Lys | Cys | Pro | Met | Gly | Phe | Ser | Tyr | Asp | Thr | Arg | Cys | |
| | 210 | | | | | 215 | | | | | 220 | | | | | |
| ttt | gac | tca | acg | gtc | act | gag | aat | gac | atc | cgt | act | gag | gag | tca | atc | 720 |
| Phe | Asp | Ser | Thr | Val | Thr | Glu | Asn | Asp | Ile | Arg | Thr | Glu | Glu | Ser | Ile | |
| 225 | | | | | 230 | | | | | 235 | | | | | 240 | |
| tac | caa | tgt | tgt | gac | ttg | gcc | ccc | gaa | gcc | aga | cag | gcc | ata | aag | tcg | 768 |
| Tyr | Gln | Cys | Cys | Asp | Leu | Ala | Pro | Glu | Ala | Arg | Gln | Ala | Ile | Lys | Ser | |
| | | | | 245 | | | | | 250 | | | | | 255 | | |
| ctc | aca | gag | cgg | ctc | tac | atc | ggg | ggt | ccc | ctg | act | aat | tca | aaa | ggg | 816 |
| Leu | Thr | Glu | Arg | Leu | Tyr | Ile | Gly | Gly | Pro | Leu | Thr | Asn | Ser | Lys | Gly | |
| | | | 260 | | | | | 265 | | | | | 270 | | | |
| cag | aac | tgc | ggt | tat | cgc | cgg | tgc | cgc | gcg | agc | ggc | gtg | ctg | acg | act | 864 |
| Gln | Asn | Cys | Gly | Tyr | Arg | Arg | Cys | Arg | Ala | Ser | Gly | Val | Leu | Thr | Thr | |
| | | 275 | | | | | 280 | | | | | 285 | | | | |
| agc | tgc | ggc | aat | acc | ctc | aca | tgc | tac | ttg | aaa | gcc | act | gcg | gcc | tgt | 912 |
| Ser | Cys | Gly | Asn | Thr | Leu | Thr | Cys | Tyr | Leu | Lys | Ala | Thr | Ala | Ala | Cys | |
| | 290 | | | | | 295 | | | | | 300 | | | | | |
| cga | gct | gca | aag | ctc | cag | gac | tgc | acg | atg | ctc | gtg | aac | gga | gac | gac | 960 |
| Arg | Ala | Ala | Lys | Leu | Gln | Asp | Cys | Thr | Met | Leu | Val | Asn | Gly | Asp | Asp | |
| 305 | | | | | 310 | | | | | 315 | | | | | 320 | |
| ctt | gtc | gtt | atc | tgc | gaa | agc | gcg | gga | acc | cag | gag | gat | gcg | gcg | agc | 1008 |
| Leu | Val | Val | Ile | Cys | Glu | Ser | Ala | Gly | Thr | Gln | Glu | Asp | Ala | Ala | Ser | |
| | | | | 325 | | | | | 330 | | | | | 335 | | |
| cta | cga | gtc | ttc | acg | gag | gct | atg | act | agg | tac | tct | gcc | ccc | ccc | ggg | 1056 |
| Leu | Arg | Val | Phe | Thr | Glu | Ala | Met | Thr | Arg | Tyr | Ser | Ala | Pro | Pro | Gly | |
| | | | 340 | | | | | 345 | | | | | 350 | | | |
| gac | ccg | ccc | caa | cca | gaa | tac | gac | ttg | gag | ctg | ata | acg | tca | tgc | tcc | 1104 |
| Asp | Pro | Pro | Gln | Pro | Glu | Tyr | Asp | Leu | Glu | Leu | Ile | Thr | Ser | Cys | Ser | |
| | | 355 | | | | | 360 | | | | | 365 | | | | |
| tcc | aat | gtg | tcg | gtc | gcg | cac | gat | gca | tcc | ggc | aaa | agg | gtg | tac | tac | 1152 |
| Ser | Asn | Val | Ser | Val | Ala | His | Asp | Ala | Ser | Gly | Lys | Arg | Val | Tyr | Tyr | |
| | 370 | | | | | 375 | | | | | 380 | | | | | |
| ctc | acc | cgt | gac | ccc | acc | acc | ccc | ctc | gca | cgg | gct | gcg | tgg | gag | aca | 1200 |
| Leu | Thr | Arg | Asp | Pro | Thr | Thr | Pro | Leu | Ala | Arg | Ala | Ala | Trp | Glu | Thr | |
| 385 | | | | | 390 | | | | | 395 | | | | | 400 | |
| gtt | aga | cac | act | cca | gtc | aac | tcc | tgg | cta | ggc | aat | atc | atc | atg | tat | 1248 |
| Val | Arg | His | Thr | Pro | Val | Asn | Ser | Trp | Leu | Gly | Asn | Ile | Ile | Met | Tyr | |
| | | | | 405 | | | | | 410 | | | | | 415 | | |
| gcg | ccc | acc | cta | tgg | gcg | agg | atg | att | ctg | atg | act | cat | ttc | ttc | tct | 1296 |
| Ala | Pro | Thr | Leu | Trp | Ala | Arg | Met | Ile | Leu | Met | Thr | His | Phe | Phe | Ser | |
| | | | 420 | | | | | 425 | | | | | 430 | | | |

```
atc ctt cta gct cag gag caa ctt gaa aaa gcc ctg gat tgt cag atc      1344
Ile Leu Leu Ala Gln Glu Gln Leu Glu Lys Ala Leu Asp Cys Gln Ile
            435                 440                 445 tac ggg gcc tgc tac tcc att gag cca ctt gac cta cct cag atc atc      1392
Tyr Gly Ala Cys Tyr Ser Ile Glu Pro Leu Asp Leu Pro Gln Ile Ile
    450                 455                 460 gaa cga ctc cat ggt ctt agc gca ttt tca ctc cat agt tac tct cca      1440
Glu Arg Leu His Gly Leu Ser Ala Phe Ser Leu His Ser Tyr Ser Pro
465                 470                 475                 480 ggt gag atc aat agg gtg gct tca tgc ctc agg aaa ctt ggg gta cca      1488
Gly Glu Ile Asn Arg Val Ala Ser Cys Leu Arg Lys Leu Gly Val Pro
                485                 490                 495 ccc ttg cga gtc tgg aga cat cgg gcc aga agt gtc cgc gct aag ttg      1536
Pro Leu Arg Val Trp Arg His Arg Ala Arg Ser Val Arg Ala Lys Leu
            500                 505                 510 ctg tcc cag ggg ggg agg gcc gcc act tgc ggc aaa tac ctc ttc aac      1584
Leu Ser Gln Gly Gly Arg Ala Ala Thr Cys Gly Lys Tyr Leu Phe Asn
        515                 520                 525 tgg gca gta agg acc aag ctt aaa ctc act cca atc ccg gct gcg tcc      1632
Trp Ala Val Arg Thr Lys Leu Lys Leu Thr Pro Ile Pro Ala Ala Ser
    530                 535                 540 cag cta gac ttg tcc ggc tgg ttc gtt gct ggt tac aac ggg gga gac      1680
Gln Leu Asp Leu Ser Gly Trp Phe Val Ala Gly Tyr Asn Gly Gly Asp
545                 550                 555                 560 ata tat cac agc ctg tct cgt gcc cga ccc cgt tgg ttc atg ttg tgc      1728
Ile Tyr His Ser Leu Ser Arg Ala Arg Pro Arg Trp Phe Met Leu Cys
                565                 570                 575 cta ctc cta ctt tct gta ggg gta ggc atc tac ctg ctc ccc aac cgg      1776
Leu Leu Leu Leu Ser Val Gly Val Gly Ile Tyr Leu Leu Pro Asn Arg
            580                 585                 590 taa                                                                  1779

<210> SEQ ID NO 4
<211> LENGTH: 592
<212> TYPE: PRT
<213> ORGANISM: Artificial sequence
<220> FEATURE:
<223> OTHER INFORMATION: sequence coding for NS5b

<400> SEQUENCE: 4

Met Ser Met Ser Tyr Thr Trp Thr Gly Ala Leu Ile Thr Pro Cys Ala
1               5                   10                  15

Ala Glu Glu Ser Lys Leu Pro Ile Asn Pro Leu Ser Asn Ser Leu Leu
            20                  25                  30

Arg His His Ser Met Val Tyr Ser Thr Thr Ser Arg Ser Ala Ser Leu
        35                  40                  45

Arg Gln Lys Lys Val Thr Phe Asp Arg Leu Gln Val Leu Asp Asp His
    50                  55                  60

Tyr Arg Asp Val Leu Lys Glu Met Lys Ala Lys Ala Ser Thr Val Lys
65                  70                  75                  80

Ala Arg Leu Leu Ser Ile Glu Glu Ala Cys Lys Leu Thr Pro Pro His
                85                  90                  95

Ser Ala Lys Ser Lys Phe Gly Tyr Gly Ala Lys Asp Val Arg Ser Leu
            100                 105                 110

Ser Ser Arg Ala Val Asn His Ile Arg Ser Val Trp Glu Asp Leu Leu
        115                 120                 125

Glu Asp Thr Glu Thr Pro Ile Asp Thr Thr Ile Met Ala Lys Asn Glu
    130                 135                 140
```

-continued

```
Val Phe Cys Val Gln Pro Glu Lys Gly Gly Arg Lys Pro Ala Arg Leu
145                 150                 155                 160

Ile Val Phe Pro Asp Leu Gly Val Arg Val Cys Glu Lys Met Ala Leu
                165                 170                 175

Tyr Asp Val Val Ser Thr Leu Pro Gln Ala Val Met Gly Pro Ser Tyr
            180                 185                 190

Gly Phe Gln Tyr Ser Pro Gly Gln Arg Val Glu Phe Leu Val Asn Thr
        195                 200                 205

Trp Lys Ser Lys Lys Cys Pro Met Gly Phe Ser Tyr Asp Thr Arg Cys
    210                 215                 220

Phe Asp Ser Thr Val Thr Glu Asn Asp Ile Arg Thr Glu Glu Ser Ile
225                 230                 235                 240

Tyr Gln Cys Cys Asp Leu Ala Pro Glu Ala Arg Gln Ala Ile Lys Ser
                245                 250                 255

Leu Thr Glu Arg Leu Tyr Ile Gly Gly Pro Leu Thr Asn Ser Lys Gly
                260                 265                 270

Gln Asn Cys Gly Tyr Arg Arg Cys Arg Ala Ser Gly Val Leu Thr Thr
            275                 280                 285

Ser Cys Gly Asn Thr Leu Thr Cys Tyr Leu Lys Ala Thr Ala Ala Cys
        290                 295                 300

Arg Ala Ala Lys Leu Gln Asp Cys Thr Met Leu Val Asn Gly Asp Asp
305                 310                 315                 320

Leu Val Val Ile Cys Glu Ser Ala Gly Thr Gln Glu Asp Ala Ala Ser
                325                 330                 335

Leu Arg Val Phe Thr Glu Ala Met Thr Arg Tyr Ser Ala Pro Pro Gly
                340                 345                 350

Asp Pro Pro Gln Pro Glu Tyr Asp Leu Glu Leu Ile Thr Ser Cys Ser
            355                 360                 365

Ser Asn Val Ser Val Ala His Asp Ala Ser Gly Lys Arg Val Tyr Tyr
        370                 375                 380

Leu Thr Arg Asp Pro Thr Thr Pro Leu Ala Arg Ala Ala Trp Glu Thr
385                 390                 395                 400

Val Arg His Thr Pro Val Asn Ser Trp Leu Gly Asn Ile Ile Met Tyr
                405                 410                 415

Ala Pro Thr Leu Trp Ala Arg Met Ile Leu Met Thr His Phe Phe Ser
                420                 425                 430

Ile Leu Leu Ala Gln Glu Gln Leu Glu Lys Ala Leu Asp Cys Gln Ile
            435                 440                 445

Tyr Gly Ala Cys Tyr Ser Ile Glu Pro Leu Asp Leu Pro Gln Ile Ile
        450                 455                 460

Glu Arg Leu His Gly Leu Ser Ala Phe Ser Leu His Ser Tyr Ser Pro
465                 470                 475                 480

Gly Glu Ile Asn Arg Val Ala Ser Cys Leu Arg Lys Leu Gly Val Pro
                485                 490                 495

Pro Leu Arg Val Trp Arg His Arg Ala Arg Ser Val Arg Ala Lys Leu
                500                 505                 510

Leu Ser Gln Gly Gly Arg Ala Ala Thr Cys Gly Lys Tyr Leu Phe Asn
            515                 520                 525

Trp Ala Val Arg Thr Lys Leu Lys Leu Thr Pro Ile Pro Ala Ala Ser
        530                 535                 540

Gln Leu Asp Leu Ser Gly Trp Phe Val Ala Gly Tyr Asn Gly Gly Asp
545                 550                 555                 560

Ile Tyr His Ser Leu Ser Arg Ala Arg Pro Arg Trp Phe Met Leu Cys
                565                 570                 575
```

```
Leu Leu Leu Leu Ser Val Gly Val Gly Ile Tyr Leu Leu Pro Asn Arg
            580                 585                 590
```

<210> SEQ ID NO 5
<211> LENGTH: 1344
<212> TYPE: DNA
<213> ORGANISM: Artificial sequence
<220> FEATURE:
<223> OTHER INFORMATION: sequence coding for NS5a
<220> FEATURE:
<221> NAME/KEY: CDS
<222> LOCATION: (1)..(1344)
<223> OTHER INFORMATION:

<400> SEQUENCE: 5

```
atg tcc ggc tcg tgg cta agg gat gtt tgg gac tgg ata tgc acg gtg      48
Met Ser Gly Ser Trp Leu Arg Asp Val Trp Asp Trp Ile Cys Thr Val
1               5                   10                  15 ttg act gac ttc aag acc tgg ctc cag tcc aag ctc ctg ccg aaa ttg      96
Leu Thr Asp Phe Lys Thr Trp Leu Gln Ser Lys Leu Leu Pro Lys Leu
                20                  25                  30 ccg gga gtc cct ttc ttc tca tgc caa cgc ggg tac aag gga gtc tgg     144
Pro Gly Val Pro Phe Phe Ser Cys Gln Arg Gly Tyr Lys Gly Val Trp
            35                  40                  45 cgg ggg gac ggc atc atg caa acc acc tgc cca tgt gga gca caa att     192
Arg Gly Asp Gly Ile Met Gln Thr Thr Cys Pro Cys Gly Ala Gln Ile
        50                  55                  60 acc gga cat gtc aaa aac ggt tcc atg agg atc gtt ggg cct aaa acc     240
Thr Gly His Val Lys Asn Gly Ser Met Arg Ile Val Gly Pro Lys Thr
65                  70                  75                  80 tgc agc aac acg tgg cac gga acg ttc ccc atc aac gcg tac acc aca     288
Cys Ser Asn Thr Trp His Gly Thr Phe Pro Ile Asn Ala Tyr Thr Thr
                85                  90                  95 ggc ccc tgc aca ccc tcc ccg gcg ccg aac tat tcc agg gcg ctg tgg     336
Gly Pro Cys Thr Pro Ser Pro Ala Pro Asn Tyr Ser Arg Ala Leu Trp
            100                 105                 110 cgg gtg gct gct gaa gag tac gtg gag att acg cgg gtg ggg gac ttc     384
Arg Val Ala Ala Glu Glu Tyr Val Glu Ile Thr Arg Val Gly Asp Phe
        115                 120                 125 cac tac gtg acg ggt atg acc acc gac aac gta aaa tgc ccg tgc cag     432
His Tyr Val Thr Gly Met Thr Thr Asp Asn Val Lys Cys Pro Cys Gln
    130                 135                 140 gtc ccg gcc ccc gaa ttc ttc act gaa ttg gac ggg gtg cgg ttg cac     480
Val Pro Ala Pro Glu Phe Phe Thr Glu Leu Asp Gly Val Arg Leu His
145                 150                 155                 160 agg tac gct ccg gcg tgc aga cct ctc cta cgg gtg gat gtc aca ttc     528
Arg Tyr Ala Pro Ala Cys Arg Pro Leu Leu Arg Val Asp Val Thr Phe
                165                 170                 175 cag gtc ggg ctc aac caa tac ctg gtt ggg tca cag ctc cca tgc gag     576
Gln Val Gly Leu Asn Gln Tyr Leu Val Gly Ser Gln Leu Pro Cys Glu
            180                 185                 190 cct gag ccg gat gtg gca gtg ctc act tcc atg ctc acc gac ccc tcc     624
Pro Glu Pro Asp Val Ala Val Leu Thr Ser Met Leu Thr Asp Pro Ser
        195                 200                 205 cac att aca gca gag acg gct aaa cgt agg ccg gcc agg ggg tct ccc     672
His Ile Thr Ala Glu Thr Ala Lys Arg Arg Pro Ala Arg Gly Ser Pro
    210                 215                 220 ccc tcc ttg gcc agc tct tca gct agc caa ttg tct gcg cct tcc ttg     720
Pro Ser Leu Ala Ser Ser Ser Ala Ser Gln Leu Ser Ala Pro Ser Leu
225                 230                 235                 240 aag gca aca tgc act acc cac cat gac tcc ccg gac gct gac ctc atc     768
Lys Ala Thr Cys Thr Thr His His Asp Ser Pro Asp Ala Asp Leu Ile
```

```
                        245                 250                 255
gag gcc aac ctc ctg tgg cgg cag gag atg ggc gga aac atc acc cgt     816
Glu Ala Asn Leu Leu Trp Arg Gln Glu Met Gly Gly Asn Ile Thr Arg
        260                 265                 270 gtg gag tca gag aat aag gtg gta att ttg gac tct ttc gac ccg ctt     864
Val Glu Ser Glu Asn Lys Val Val Ile Leu Asp Ser Phe Asp Pro Leu
        275                 280                 285 cga gcg gaa gag gat gag agg gaa gta tcc gtt gca gca gag atc ctg     912
Arg Ala Glu Glu Asp Glu Arg Glu Val Ser Val Ala Ala Glu Ile Leu
        290                 295                 300 cga aaa tcc aag aag ttc ccc ccc gcg ttg ccc ata tgg gca cgc ccg     960
Arg Lys Ser Lys Lys Phe Pro Pro Ala Leu Pro Ile Trp Ala Arg Pro
305                 310                 315                 320 gat tac aac cct cca ctg tta gag tcc tgg aaa agt ccg gac tac gtc    1008
Asp Tyr Asn Pro Pro Leu Leu Glu Ser Trp Lys Ser Pro Asp Tyr Val
                325                 330                 335 cct ccg gcg gtg cat ggg tgc cca ttg ccg cct acc acg ggc cct cca    1056
Pro Pro Ala Val His Gly Cys Pro Leu Pro Pro Thr Thr Gly Pro Pro
                340                 345                 350 ata ccg cct cca cgg aaa aag agg acg gtt gtt ctg aca gag tcc acc    1104
Ile Pro Pro Pro Arg Lys Lys Arg Thr Val Val Leu Thr Glu Ser Thr
                355                 360                 365 gtg tct tct gcc ttg gcg gag ctg gct act aag act ttc ggc agc tcc    1152
Val Ser Ser Ala Leu Ala Glu Leu Ala Thr Lys Thr Phe Gly Ser Ser
370                 375                 380 gga tcg tcg gcc gtt gac agc ggc acg gcg acc gcc cct ccc gat cag    1200
Gly Ser Ser Ala Val Asp Ser Gly Thr Ala Thr Ala Pro Pro Asp Gln
385                 390                 395                 400 acc tct gac gac ggt gac aaa gaa tct gac att gag tcg tac tcc tcc    1248
Thr Ser Asp Asp Gly Asp Lys Glu Ser Asp Ile Glu Ser Tyr Ser Ser
                405                 410                 415 atg ccc ccc ctt gag ggg gag ccg ggg gac cct gat ctc agc gac ggg    1296
Met Pro Pro Leu Glu Gly Glu Pro Gly Asp Pro Asp Leu Ser Asp Gly
                420                 425                 430 tct tgg tct acc gtg agc ggg gag gcc ggc gac gac atc gtc tgc tgc    1344
Ser Trp Ser Thr Val Ser Gly Glu Ala Gly Asp Asp Ile Val Cys Cys
            435                 440                 445

<210> SEQ ID NO 6
<211> LENGTH: 448
<212> TYPE: PRT
<213> ORGANISM: Artificial sequence
<220> FEATURE:
<223> OTHER INFORMATION: sequence coding for NS5a

<400> SEQUENCE: 6

Met Ser Gly Ser Trp Leu Arg Asp Val Trp Asp Trp Ile Cys Thr Val
1               5                   10                  15

Leu Thr Asp Phe Lys Thr Trp Leu Gln Ser Lys Leu Leu Pro Lys Leu
                20                  25                  30

Pro Gly Val Pro Phe Phe Ser Cys Gln Arg Gly Tyr Lys Gly Val Trp
            35                  40                  45

Arg Gly Asp Gly Ile Met Gln Thr Thr Cys Pro Cys Gly Ala Gln Ile
        50                  55                  60

Thr Gly His Val Lys Asn Gly Ser Met Arg Ile Val Gly Pro Lys Thr
65                  70                  75                  80

Cys Ser Asn Thr Trp His Gly Thr Phe Pro Ile Asn Ala Tyr Thr Thr
                85                  90                  95

Gly Pro Cys Thr Pro Ser Pro Ala Pro Asn Tyr Ser Arg Ala Leu Trp
            100                 105                 110
```

Arg Val Ala Ala Glu Glu Tyr Val Glu Ile Thr Arg Val Gly Asp Phe
        115                 120                 125

His Tyr Val Thr Gly Met Thr Thr Asp Asn Val Lys Cys Pro Cys Gln
130                 135                 140

Val Pro Ala Pro Glu Phe Phe Thr Glu Leu Asp Gly Val Arg Leu His
145                 150                 155                 160

Arg Tyr Ala Pro Ala Cys Arg Pro Leu Leu Arg Val Asp Val Thr Phe
                165                 170                 175

Gln Val Gly Leu Asn Gln Tyr Leu Val Gly Ser Gln Leu Pro Cys Glu
            180                 185                 190

Pro Glu Pro Asp Val Ala Val Leu Thr Ser Met Leu Thr Asp Pro Ser
        195                 200                 205

His Ile Thr Ala Glu Thr Ala Lys Arg Arg Pro Ala Arg Gly Ser Pro
210                 215                 220

Pro Ser Leu Ala Ser Ser Ala Ser Gln Leu Ser Ala Pro Ser Leu
225                 230                 235                 240

Lys Ala Thr Cys Thr Thr His His Asp Ser Pro Asp Ala Asp Leu Ile
                245                 250                 255

Glu Ala Asn Leu Leu Trp Arg Gln Glu Met Gly Gly Asn Ile Thr Arg
            260                 265                 270

Val Glu Ser Glu Asn Lys Val Val Ile Leu Asp Ser Phe Asp Pro Leu
        275                 280                 285

Arg Ala Glu Glu Asp Glu Arg Glu Val Ser Val Ala Ala Glu Ile Leu
    290                 295                 300

Arg Lys Ser Lys Lys Phe Pro Pro Ala Leu Pro Ile Trp Ala Arg Pro
305                 310                 315                 320

Asp Tyr Asn Pro Pro Leu Leu Glu Ser Trp Lys Ser Pro Asp Tyr Val
                325                 330                 335

Pro Pro Ala Val His Gly Cys Pro Leu Pro Pro Thr Thr Gly Pro Pro
            340                 345                 350

Ile Pro Pro Pro Arg Lys Lys Arg Thr Val Val Leu Thr Glu Ser Thr
        355                 360                 365

Val Ser Ser Ala Leu Ala Glu Leu Ala Thr Lys Thr Phe Gly Ser Ser
    370                 375                 380

Gly Ser Ser Ala Val Asp Ser Gly Thr Ala Thr Ala Pro Pro Asp Gln
385                 390                 395                 400

Thr Ser Asp Asp Gly Asp Lys Glu Ser Asp Ile Glu Ser Tyr Ser Ser
                405                 410                 415

Met Pro Pro Leu Glu Gly Glu Pro Gly Asp Pro Asp Leu Ser Asp Gly
            420                 425                 430

Ser Trp Ser Thr Val Ser Gly Glu Ala Gly Asp Asp Ile Val Cys Cys
        435                 440                 445

<210> SEQ ID NO 7
<211> LENGTH: 2241
<212> TYPE: DNA
<213> ORGANISM: Artificial sequence
<220> FEATURE:
<223> OTHER INFORMATION: sequence coding for CE1E2
<220> FEATURE:
<221> NAME/KEY: CDS
<222> LOCATION: (1)..(2241)
<223> OTHER INFORMATION:

<400> SEQUENCE: 7 atg agc aca aat cct aaa cct caa aga aaa acc aaa cgt aac acc aac    48
Met Ser Thr Asn Pro Lys Pro Gln Arg Lys Thr Lys Arg Asn Thr Asn -continued

```
            1               5              10              15
cgc cgc cca cag gac gtt aag ttc ccg ggc ggt ggt cag atc gtt ggt      96
Arg Arg Pro Gln Asp Val Lys Phe Pro Gly Gly Gly Gln Ile Val Gly
                 20              25              30 gga gtt tac ctg ttg ccg cgc agg ggc ccc agg ttg ggt gtg cgc gcg     144
Gly Val Tyr Leu Leu Pro Arg Arg Gly Pro Arg Leu Gly Val Arg Ala
         35              40              45 act agg aag act tcc gag cgg tcg caa cct cgt gga agg cga caa cct     192
Thr Arg Lys Thr Ser Glu Arg Ser Gln Pro Arg Gly Arg Arg Gln Pro
 50              55              60 atc ccc aag gct cgc cgg ccc gag ggt agg acc tgg gct cag ccc ggg     240
Ile Pro Lys Ala Arg Arg Pro Glu Gly Arg Thr Trp Ala Gln Pro Gly
65              70              75              80 tac cct tgg ccc ctc tat ggc aac gag ggt atg ggg tgg gca gga tgg     288
Tyr Pro Trp Pro Leu Tyr Gly Asn Glu Gly Met Gly Trp Ala Gly Trp
                 85              90              95 ctc ctg tca ccc cgt ggc tct cgg cct agt tgg ggc ccc aca gac ccc     336
Leu Leu Ser Pro Arg Gly Ser Arg Pro Ser Trp Gly Pro Thr Asp Pro
        100             105             110 cgg cgt agg tcg cgt aat ttg ggt aag gtc atc gat acc ctt aca tgc     384
Arg Arg Arg Ser Arg Asn Leu Gly Lys Val Ile Asp Thr Leu Thr Cys
        115             120             125 ggc ttc gcc gac ctc atg ggg tac att ccg ctt gtc ggc gcc ccc cta     432
Gly Phe Ala Asp Leu Met Gly Tyr Ile Pro Leu Val Gly Ala Pro Leu
130             135             140 gga ggc gct gcc agg gcc ctg gcg cat ggc gtc cgg gtt ctg gag gac     480
Gly Gly Ala Ala Arg Ala Leu Ala His Gly Val Arg Val Leu Glu Asp
145             150             155             160 ggc gtg aac tat gca aca ggg aat ctg ccc ggt tgc tct ttc tct atc     528
Gly Val Asn Tyr Ala Thr Gly Asn Leu Pro Gly Cys Ser Phe Ser Ile
                165             170             175 ttc ctc tta gct ttg ctg tct tgt ttg acc atc cca gct tcc gct tac     576
Phe Leu Leu Ala Leu Leu Ser Cys Leu Thr Ile Pro Ala Ser Ala Tyr
        180             185             190 gag gtg cgc aac gtg tcc ggg ata tac cat gtc acg aac gac tgc tcc     624
Glu Val Arg Asn Val Ser Gly Ile Tyr His Val Thr Asn Asp Cys Ser
        195             200             205 aac tca agt att gtg tat gag gca gcg gac atg atc atg cac acc ccc     672
Asn Ser Ser Ile Val Tyr Glu Ala Ala Asp Met Ile Met His Thr Pro
210             215             220 ggg tgc gtg ccc tgc gtc cgg gag agt aat ttc tcc cgt tgc tgg gta     720
Gly Cys Val Pro Cys Val Arg Glu Ser Asn Phe Ser Arg Cys Trp Val
225             230             235             240 gcg ctc act ccc acg ctc gcg gcc agg aac agc agc atc ccc acc acg     768
Ala Leu Thr Pro Thr Leu Ala Ala Arg Asn Ser Ser Ile Pro Thr Thr
                245             250             255 aca ata cga cgc cac gtc gat ttg ctc gtt ggg gcg gct gct ctc tgt     816
Thr Ile Arg Arg His Val Asp Leu Leu Val Gly Ala Ala Ala Leu Cys
        260             265             270 tcc gct atg tac gtt ggg gat ctc tgc gga tcc gtt ttt ctc gtc tcc     864
Ser Ala Met Tyr Val Gly Asp Leu Cys Gly Ser Val Phe Leu Val Ser
        275             280             285 cag ctg ttc acc ttc tca cct cgc cgg tat gag acg gta caa gat tgc     912
Gln Leu Phe Thr Phe Ser Pro Arg Arg Tyr Glu Thr Val Gln Asp Cys
        290             295             300 aat tgc tca atc tat ccc ggc cac gta tca ggt cac cgc atg gct tgg     960
Asn Cys Ser Ile Tyr Pro Gly His Val Ser Gly His Arg Met Ala Trp
305             310             315             320 gat atg atg atg aac tgg tca cct aca acg gcc cta gtg gta tcg cag    1008
Asp Met Met Met Asn Trp Ser Pro Thr Thr Ala Leu Val Val Ser Gln
```

-continued

```
                  325                 330                 335
cta ctc cgg atc cca caa gcc gtc gtg gac atg gtg gcg ggg gcc cac   1056
Leu Leu Arg Ile Pro Gln Ala Val Val Asp Met Val Ala Gly Ala His
            340                 345                 350 tgg ggt gtc cta gcg ggc ctt gcc tac tat tcc atg gtg ggg aac tgg   1104
Trp Gly Val Leu Ala Gly Leu Ala Tyr Tyr Ser Met Val Gly Asn Trp
        355                 360                 365 gct aag gtc ttg att gtg atg cta ctc ttt gct ggc gtt gac ggg cac   1152
Ala Lys Val Leu Ile Val Met Leu Leu Phe Ala Gly Val Asp Gly His
    370                 375                 380 acc cac gtg aca ggg gga agg gta gcc tcc agc acc cag agc ctc gtg   1200
Thr His Val Thr Gly Gly Arg Val Ala Ser Ser Thr Gln Ser Leu Val
385                 390                 395                 400 tcc tgg ctc tca caa ggg cca tct cag aaa atc caa ctc gtg aac acc   1248
Ser Trp Leu Ser Gln Gly Pro Ser Gln Lys Ile Gln Leu Val Asn Thr
                405                 410                 415 aac ggc agc tgg cac atc aac agg acc gct ctg aat tgc aat gac tcc   1296
Asn Gly Ser Trp His Ile Asn Arg Thr Ala Leu Asn Cys Asn Asp Ser
            420                 425                 430 ctc caa act ggg ttc att gct gcg ctg ttc tac gca cac agg ttc aac   1344
Leu Gln Thr Gly Phe Ile Ala Ala Leu Phe Tyr Ala His Arg Phe Asn
        435                 440                 445 gcg tcc gga tgt cca gag cgc atg gcc agc tgc cgc ccc atc gac aag   1392
Ala Ser Gly Cys Pro Glu Arg Met Ala Ser Cys Arg Pro Ile Asp Lys
    450                 455                 460 ttc gct cag ggg tgg ggt ccc atc act cac gtt gtg cct aac atc tcg   1440
Phe Ala Gln Gly Trp Gly Pro Ile Thr His Val Val Pro Asn Ile Ser
465                 470                 475                 480 gac cag agg cct tat tgc tgg cac tat gca ccc caa ccg tgc ggt att   1488
Asp Gln Arg Pro Tyr Cys Trp His Tyr Ala Pro Gln Pro Cys Gly Ile
                485                 490                 495 gta ccc gcg tcg cag gtg tgt ggc cca gtg tat tgc ttc acc ccg agt   1536
Val Pro Ala Ser Gln Val Cys Gly Pro Val Tyr Cys Phe Thr Pro Ser
            500                 505                 510 cct gtt gtg gtg ggg acg acc gac cgt tcc gga gtc ccc acg tat agc   1584
Pro Val Val Val Gly Thr Thr Asp Arg Ser Gly Val Pro Thr Tyr Ser
        515                 520                 525 tgg ggg gag aat gag aca gac gtg ctg cta ctc aac aac acg cgg ccg   1632
Trp Gly Glu Asn Glu Thr Asp Val Leu Leu Leu Asn Asn Thr Arg Pro
    530                 535                 540 ccg caa ggc aac tgg ttc ggc tgt aca tgg atg aat agc acc ggg ttc   1680
Pro Gln Gly Asn Trp Phe Gly Cys Thr Trp Met Asn Ser Thr Gly Phe
545                 550                 555                 560 acc aag acg tgc ggg ggc ccc ccg tgt aac atc ggg ggg gtt ggc aac   1728
Thr Lys Thr Cys Gly Gly Pro Pro Cys Asn Ile Gly Gly Val Gly Asn
                565                 570                 575 aac acc ttg att tgc ccc acg gat tgc ttc cga aag cac ccc gag gcc   1776
Asn Thr Leu Ile Cys Pro Thr Asp Cys Phe Arg Lys His Pro Glu Ala
            580                 585                 590 act tac acc aaa tgc ggc tcg ggt cct tgg ttg aca cct agg tgt cta   1824
Thr Tyr Thr Lys Cys Gly Ser Gly Pro Trp Leu Thr Pro Arg Cys Leu
        595                 600                 605 gtt gac tac cca tac aga ctt tgg cac tac ccc tgc act atc aat ttt   1872
Val Asp Tyr Pro Tyr Arg Leu Trp His Tyr Pro Cys Thr Ile Asn Phe
    610                 615                 620 acc atc ttc aag gtc agg atg tac gtg ggg ggc gtg gag cac agg ctc   1920
Thr Ile Phe Lys Val Arg Met Tyr Val Gly Gly Val Glu His Arg Leu
625                 630                 635                 640 aac gcc gcg tgc aat tgg acc cga gga gag cgc tgt gac ctg gag gac   1968
Asn Ala Ala Cys Asn Trp Thr Arg Gly Glu Arg Cys Asp Leu Glu Asp
```

```
                645                 650                 655
agg gat aga tca gag ctt agc ccg ctg cta ttg tct aca acg gag tgg    2016
Arg Asp Arg Ser Glu Leu Ser Pro Leu Leu Leu Ser Thr Thr Glu Trp
            660                 665                 670 cag gta ctg ccc tgt tcc ttt acc acc cta ccg gct ctg tcc act gga    2064
Gln Val Leu Pro Cys Ser Phe Thr Thr Leu Pro Ala Leu Ser Thr Gly
        675                 680                 685 ttg atc cac ctc cat cag aat atc gtg gac gtg caa tac ctg tac ggt    2112
Leu Ile His Leu His Gln Asn Ile Val Asp Val Gln Tyr Leu Tyr Gly
    690                 695                 700 gta ggg tca gtg gtt gtc tcc gtc gta atc aaa tgg gag tat gtt ctg    2160
Val Gly Ser Val Val Val Ser Val Val Ile Lys Trp Glu Tyr Val Leu
705                 710                 715                 720 ctc ctc ttc ctt ctc ctg gcg gac gcg cgc gtc tgt gcc tgc ttg tgg    2208
Leu Leu Phe Leu Leu Leu Ala Asp Ala Arg Val Cys Ala Cys Leu Trp
                725                 730                 735 atg atg ctg ctg ata gcc cag gct gag gcc tga                        2241
Met Met Leu Leu Ile Ala Gln Ala Glu Ala
                740                 745

<210> SEQ ID NO 8
<211> LENGTH: 746
<212> TYPE: PRT
<213> ORGANISM: Artificial sequence
<220> FEATURE:
<223> OTHER INFORMATION: sequence coding for CE1E2

<400> SEQUENCE: 8

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Met Ile Met His Thr Pro
    210                 215                 220

Gly Cys Val Pro Cys Val Arg Glu Ser Asn Phe Ser Arg Cys Trp Val
225                 230                 235                 240
```

```
Ala Leu Thr Pro Thr Leu Ala Ala Arg Asn Ser Ser Ile Pro Thr Thr
                245                 250                 255

Thr Ile Arg Arg His Val Asp Leu Leu Val Gly Ala Ala Ala Leu Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg Tyr Glu Thr Val Gln Asp Cys
    290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly His
    370                 375                 380

Thr His Val Thr Gly Gly Arg Val Ala Ser Ser Thr Gln Ser Leu Val
385                 390                 395                 400

Ser Trp Leu Ser Gln Gly Pro Ser Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu Gln Thr Gly Phe Ile Ala Ala Leu Phe Tyr Ala His Arg Phe Asn
        435                 440                 445

Ala Ser Gly Cys Pro Glu Arg Met Ala Ser Cys Arg Pro Ile Asp Lys
    450                 455                 460

Phe Ala Gln Gly Trp Gly Pro Ile Thr His Val Val Pro Asn Ile Ser
465                 470                 475                 480

Asp Gln Arg Pro Tyr Cys Trp His Tyr Ala Pro Gln Pro Cys Gly Ile
                485                 490                 495

Val Pro Ala Ser Gln Val Cys Gly Pro Val Tyr Cys Phe Thr Pro Ser
            500                 505                 510

Pro Val Val Val Gly Thr Thr Asp Arg Ser Gly Val Pro Thr Tyr Ser
        515                 520                 525

Trp Gly Glu Asn Glu Thr Asp Val Leu Leu Leu Asn Asn Thr Arg Pro
    530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Val Gly Asn
                565                 570                 575

Asn Thr Leu Ile Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
        595                 600                 605

Val Asp Tyr Pro Tyr Arg Leu Trp His Tyr Pro Cys Thr Ile Asn Phe
    610                 615                 620

Thr Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
```

```
                    660               665                670
Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
            690                 695                 700

Val Gly Ser Val Val Ser Val Val Ile Lys Trp Glu Tyr Val Leu
705                 710                 715                 720

Leu Leu Phe Leu Leu Leu Ala Asp Ala Arg Val Cys Ala Cys Leu Trp
                725                 730                 735

Met Met Leu Leu Ile Ala Gln Ala Glu Ala
                740                 745

<210> SEQ ID NO 9
<211> LENGTH: 29
<212> TYPE: DNA
<213> ORGANISM: Artificial sequence
<220> FEATURE:
<223> OTHER INFORMATION: primer oIV166

<400> SEQUENCE: 9
gggggggcta tggcgcctat cacggccta                                    29

<210> SEQ ID NO 10
<211> LENGTH: 32
<212> TYPE: DNA
<213> ORGANISM: Artificial sequence
<220> FEATURE:
<223> OTHER INFORMATION: primer oIV171

<400> SEQUENCE: 10 gggggggacgc gtttagcatg gcgtggagca gt                               32

<210> SEQ ID NO 11
<211> LENGTH: 30
<212> TYPE: DNA
<213> ORGANISM: Artificial sequence
<220> FEATURE:
<223> OTHER INFORMATION: primer oIV232

<400> SEQUENCE: 11 gggggggagat ctccagcagg cagaagtatg                                  30

<210> SEQ ID NO 12
<211> LENGTH: 33
<212> TYPE: DNA
<213> ORGANISM: Artificial sequence
<220> FEATURE:
<223> OTHER INFORMATION: primer oIV233

<400> SEQUENCE: 12
gggggggtcg accgaaaatg gatatacaag ctc                               33

<210> SEQ ID NO 13
<211> LENGTH: 35
<212> TYPE: DNA
<213> ORGANISM: Artificial sequence
<220> FEATURE:
<223> OTHER INFORMATION: primer oIV212

<400> SEQUENCE: 13 gggggggtcta gaatgtcaat gtcctacaca tggac                            35

<210> SEQ ID NO 14
<211> LENGTH: 32
```

<212> TYPE: DNA
<213> ORGANISM: Artificial sequence
<220> FEATURE:
<223> OTHER INFORMATION: primer oIV218

<400> SEQUENCE: 14 gggggggtcta gattaccggt tgggagcag gt                32

<210> SEQ ID NO 15
<211> LENGTH: 32
<212> TYPE: DNA
<213> ORGANISM: Artificial sequence
<220> FEATURE:
<223> OTHER INFORMATION: primer oIV225

<400> SEQUENCE: 15 gggggggctgc agatggcgcc tatcacggcc ta                32

<210> SEQ ID NO 16
<211> LENGTH: 32
<212> TYPE: DNA
<213> ORGANISM: Artificial sequence
<220> FEATURE:
<223> OTHER INFORMATION: primer oIV226

<400> SEQUENCE: 16 gggggggtcta gattagcatg gcgtggagca gt                32

<210> SEQ ID NO 17
<211> LENGTH: 35
<212> TYPE: DNA
<213> ORGANISM: Artificial sequence
<220> FEATURE:
<223> OTHER INFORMATION: primer oIV227

<400> SEQUENCE: 17 ggggggggtcg acatgtcaat gtcctacaca tggac                35

<210> SEQ ID NO 18
<211> LENGTH: 32
<212> TYPE: DNA
<213> ORGANISM: Artificial sequence
<220> FEATURE:
<223> OTHER INFORMATION: primer oIV228

<400> SEQUENCE: 18 ggggggggcat gcttaccggt tgggagcag gt                32

<210> SEQ ID NO 19
<211> LENGTH: 33
<212> TYPE: DNA
<213> ORGANISM: Artificial sequence
<220> FEATURE:
<223> OTHER INFORMATION: primer oIV229

<400> SEQUENCE: 19 gggggggtcta gaccggtagt tcgcatatac ata                33

<210> SEQ ID NO 20
<211> LENGTH: 33
<212> TYPE: DNA
<213> ORGANISM: Artificial sequence
<220> FEATURE:
<223> OTHER INFORMATION: primer oIV172

<400> SEQUENCE: 20 gggggggggta ccatgtccgg ctcgtggcta agg                33

<210> SEQ ID NO 21
<211> LENGTH: 33
<212> TYPE: DNA
<213> ORGANISM: Artificial sequence
<220> FEATURE:
<223> OTHER INFORMATION: primer oIV173

<400> SEQUENCE: 21 gggggggtcta gattagcagc agacgatgtc gtc         33

<210> SEQ ID NO 22
<211> LENGTH: 33
<212> TYPE: DNA
<213> ORGANISM: Artificial sequence
<220> FEATURE:
<223> OTHER INFORMATION: primer oIV62

<400> SEQUENCE: 22 ggggggggcta gcatgagcac aaatcctaaa cct         33

<210> SEQ ID NO 23
<211> LENGTH: 33
<212> TYPE: DNA
<213> ORGANISM: Artificial sequence
<220> FEATURE:
<223> OTHER INFORMATION: primer oIV68

<400> SEQUENCE: 23 gggggggtcta gatcaggcct cagcctgggc tat         33

<210> SEQ ID NO 24
<211> LENGTH: 10
<212> TYPE: PRT
<213> ORGANISM: Artificial sequence
<220> FEATURE:
<223> OTHER INFORMATION: epitope GLL

<400> SEQUENCE: 24

Gly Leu Leu Gly Cys Ile Ile Thr Ser Leu
1               5                   10

<210> SEQ ID NO 25
<211> LENGTH: 9
<212> TYPE: PRT
<213> ORGANISM: Artificial sequence
<220> FEATURE:
<223> OTHER INFORMATION: epitope ALY

<400> SEQUENCE: 25

Ala Leu Tyr Asp Val Val Ser Thr Leu
1               5

<210> SEQ ID NO 26
<211> LENGTH: 9
<212> TYPE: PRT
<213> ORGANISM: Artificial sequence
<220> FEATURE:
<223> OTHER INFORMATION: epitope KLQ

<400> SEQUENCE: 26

Lys Leu Gln Asp Cys Thr Met Leu Val
1               5

<210> SEQ ID NO 27
<211> LENGTH: 9
<212> TYPE: PRT

```
<213> ORGANISM: Artificial sequence
<220> FEATURE:
<223> OTHER INFORMATION: epitope DLM

<400> SEQUENCE: 27

Asp Leu Met Gly Tyr Ile Pro Leu Val
1               5
```